(12) United States Patent
Benaron et al.

(10) Patent No.: US 6,711,426 B2
(45) Date of Patent: Mar. 23, 2004

(54) SPECTROSCOPY ILLUMINATOR WITH IMPROVED DELIVERY EFFICIENCY FOR HIGH OPTICAL DENSITY AND REDUCED THERMAL LOAD

(75) Inventors: David A. Benaron, Portola Valley, CA (US); Ilian H. Parachikov, Fremont, CA (US)

(73) Assignee: Spectros Corporation, Portola Valley, CA (US)

( * ) Notice: Subject to any disclaimer, the term of this patent is extended or adjusted under 35 U.S.C. 154(b) by 0 days.

(21) Appl. No.: 10/119,998

(22) Filed: Apr. 9, 2002

(65) Prior Publication Data

US 2003/0191379 A1 Oct. 9, 2003

(51) Int. Cl.[7] .............................. A61B 5/00; A61B 1/06
(52) U.S. Cl. .................. 600/342; 600/478; 362/572
(58) Field of Search ................... 600/310, 342, 600/476, 478; 362/551, 555, 572; 385/12, 14, 33; 606/2; 607/88

(56) References Cited

U.S. PATENT DOCUMENTS

| 29,304 A | 7/1860 | Pratt | |
|---|---|---|---|
| 4,660,974 A | * 4/1987 | Machler et al. | 356/328 |
| 5,280,788 A | 1/1994 | Janes et al. | |
| 5,355,425 A | * 10/1994 | Braiman et al. | 385/12 |
| 5,645,059 A | 7/1997 | Fein et al. | |
| 5,901,261 A | * 5/1999 | Wach | 385/33 |
| 5,931,779 A | 8/1999 | Arakaki et al. | |
| 5,941,822 A | 8/1999 | Skladnev et al. | |
| 5,974,210 A | 10/1999 | Alcock et al. | |
| 6,251,068 B1 | 6/2001 | Akiba et al. | |
| 6,252,254 B1 | 6/2001 | Soules et al. | |

FOREIGN PATENT DOCUMENTS

WO    WO 00/01295    1/2000

* cited by examiner

*Primary Examiner*—Eric F. Winakur
(74) *Attorney, Agent, or Firm*—Dorsey & Whitney LLP

(57) ABSTRACT

An improved illuminator for generating broadband light, and for delivering the light to a sample with an improved delivery efficiency, for higher optical density and/or reduced thermal transfer, than achieved with conventional halogen bulb sources. The illuminator enables spectroscopic analysis in thermally-sensitive or spatially-constrained environments. A phosphor-coated broadband white LED and integrated collimating optics produces a continuous, collimated broadband light beam from 400 nm to 700 nm, which is then transmitted through space to a sample region, such as a living tissue in vivo. This results in a high net efficient delivery of light to the tissue sample. An efficient conversion of power to light, and the high delivery efficiency, keeps both the illuminator and sample cool during operation, allowing the illuminator to be integrated into the tip of a medical probe or into monitoring systems.

32 Claims, 7 Drawing Sheets

SPECTROSCOPY ILLUMINATOR WITH IMPROVED DELIVERY EFFICIENCY FOR HIGH OPTICAL DENSITY AND REDUCED THERMAL LOAD

FIELD OF THE INVENTION

The present invention relates to illumination devices and systems for providing a high efficiency of broadband light delivery to thermally-sensitive or spatially-constrained environments, and more particularly relates to the embedding of a light source comprised of a white, conversion-efficient, narrow-angle, light emitting diode with integrated collimating and light collection optics into a medical catheter for indwelling gastrointestinal placement for the purpose of performing real-time in vivo tissue oxygenation measurements of mucosal surfaces via visible wavelength optical spectroscopy, thus avoiding some of the cost, risk, light level limitations inherent in conventional illuminator systems.

BACKGROUND OF THE INVENTION

The traditional broadband light sources for optical spectroscopy in the near UV, visible, and/or near-infrared wavelengths are the fluorescent, incandescent, and arc-lamp bulbs. Typically, spectroscopy bulb is optically coupled to the test sample via gratings, lenses, fibers, and/or free-space transfer. However, such traditional light sources have significant native disadvantages, including that: (a) they produce their light rather inefficiently, wasting a large proportion of the power supplied to them as heat and unusable wavelengths of light. This is a drawback in devices where significant local heating (such as medical devices in contact with tissue) or high power consumption (such as battery operated devices for field use) are undesirable or unacceptable, and (b) they emit light over a wide spherical angle from non-point sources, rendering inefficient any attempts to direct their light either onto spectroscopy samples (such as living tissue) or into optical delivery systems (such as fibers coupled to test samples), which in turn further raises heat production and power consumption for any desired level of sample illumination.

These limitations are best appreciated by example. First, with specific regard to the production of large amounts of heat, conventional bulbs are inefficient at best. The visible light output from a conventional incandescent light bulb represents only 4% of the total power consumed by the bulb. This conversion efficiency rises to only 14% for so-called high-output halogen lamps (though the improved efficiency results in accelerated drift and bulb aging). These efficiencies can easily drop farther, by a factor of 5 or more, if one considers only in-band light used in spectroscopic analysis (e.g., a 500–600 nm light band for hemoglobin analysis) in determination of the conversion efficiency.

The physical reason for this meager rate of energy conversion is that tungsten filaments, as well as heated arc lamp electrodes, operate as blackbody thermal radiators, and thus radiate mostly infrared radiation, plus a small component of UV radiation, at any temperature they can withstand. While in theory an ideal blackbody radiator produces visible light most efficiently at 6,600 K (11,500° F.), nothing known in the art remains solid for use as a filament at this temperature, which exceeds the temperature at the sun's surface. Even so-called "high-efficiency" projection-type halogen lamps must therefore operate far below this ideal temperature, often operating instead from 2,700 K to 3,500 K (just below Tungsten's melting point of 3,683 K). As a result, such bulbs typically require 6.9 W of power to produce 5.9 W of heat, in addition to 1.0 W of light.

Such poor conversion efficiencies result in a high degree of unwanted thermal output, making conventional bulbs run hot, and in turn preventing close illumination of the sample and often relegating bulb-based light sources into fiber-coupled hot, external, fan-cooled boxes.

Second, with regard to the broad spatial emission, conventional bulbs typically produce light in all directions in the absence of mirrors or lenses—that is, relatively uniformly over a full $4\pi$ spherical angle. Further, because a filament has a length and width, the light can no longer be focused to a point. This broad spatial emission typically makes a direct coupling of light from a conventional bulb onto a sample, or into an optical guide, inefficient. For illustration, consider a 1 cm diameter spherical bulb in which light from the bulb's filament radiates evenly in all directions. The glass surface resides approximately 5 mm from the filament in all directions, for a surface area of the glass sphere of $4/3*\pi*r^2$, or 105 mm$^2$. The portion of this uniform field of radiated light reaching a 1 mm diameter sample, placed up against the bulb glass, measures only 0.79 mm$^2$. Thus, this tiny sample intercepts (and is thus illuminated by) only 0.2% of the total light output from the bulb, as given by the ratio (0.79 mm$^2$/105 mm$^2$), with 99.8% of the bulbs output wasted. The less compact a lamp's source, the more difficult it becomes to focus and guide its light. This is especially true for UV fluorescent lamps, where focusing losses are far higher than for a halogen bulb.

Further, the surface temperature of a halogen bulb often exceeds 120° C. making a close approximation of a hot bulb and sample not wise or practical in many cases, especially if the sample is living or fragile. Moving the sample away from the bulb, in order to spare the sample from heating, only worsens the inefficiencies described above. Nor is the situation improved by separating the bulb and sample using optical fiber. Directly attaching an optical fiber to the glass or quartz surface of 1 cm diameter bulb discussed above (such as by using optical glue) allows the fiber to intercept and capture only those photons striking the face of the fiber. A fiber measuring only 100 microns in diameter has a tiny face area measuring just 0.0079 mm$^2$. Thus, a 100 micron fiber, glued to the bulb 5 mm from the filament, collects only 0.002% of the bulb's emitted light, as given by the ratio (0.0079 mm$^2$/105 mm$^2$). Even if the diameter of the fiber in this example were to be enlarged 10 fold, this transfer ratio would rise to only 0.2% of the bulb's visible light output that is intercepted and transmitted to the sample, again with 99.8% of the bulbs output lost and wasted.

All told, when taking into consideration both of the above limitations, the poor conversion efficiency of energy to light and the poor transfer efficiency of light to the sample, only 0.0003% of the energy flowing into the 1 cm bulb discussed above ends up converted to visible light, captured, and successfully transmitted by a fiber to a tissue sample, for more than 99.9997% of the total light wasted. Here, we term the 0.0003% figure of merit the delivered efficiency. Another way of expressing how poor this net delivered efficiency is, in fact, is that for the preceding bare-fiber-to-bare-bulb example, 369,524 watts of energy would have been required by the bulb for each watt of light delivered to sample or tissue, with the remainder released and lost as heat. These limitations of conventional sources are apparent in the art.

Broadband lamp sources or lamp designs are known, and are used for spectroscopy. Most art regarding illumination sources for spectroscopy suggest devices or methods that describe conventional light sources, although some describe more exotic lamp sources (e.g., U.S. Pat. No. RE. 29,304). White LEDs are known (e.g., U.S. Pat. No. 6,252,254, WO 01/01070), however none are suggested as spectroscopic light sources, and their high conversion efficiency, narrow angle of emission, and optical stability have not been cited nor exploited for spectroscopy purposes, especially in medicine for in vivo uses, save merely that they have been mentioned in passing for the purpose of general non-spectroscopic endoscopic illumination (U.S. Pat. No. 6,251,068). Several schemes for reducing heat production or for transmitting light to a sample are known (e.g., such as light conducting rods in U.S. Pat. No. 5,974,210), but none with the purpose of improving the efficiency of delivery, nor are these sources specifically designed to operate as cool spectroscopic illuminators with high delivery efficiency.

With specific regard to medical probes coupled to or embedded with light sources, a number of systems are known. Examples include invasive or tissue surface monitoring devices equipped with fiber optics, such as catheters, needles, and trocars (e.g., U.S. Pat. Nos. 5,280,788, 5,931,779), as well devices containing the light source itself (e.g., U.S. Pat. Nos. 5,645,059, 5,941,822, WO 00/01295). These systems typically completely ignore the complex issues of broadband illumination source design, suggesting only that known or existing light sources can be used rather than proposing improved illumination sources, and none of these systems consider specifically design issues regarding design and deployment of broadband optical light sources, especially with regard to conversion efficiency, source efficiency, and heat transfer to the sample, nor do they propose any specific or novel high delivery efficient optical sources.

Therefore, all of the above illumination systems and methods suffer from one or more limitations noted above, in that they are either narrow band emitters (such as lasers or filtered spectra), they are not configured to deliver light with a high efficiency, they have obligatory high local heating of the sample, they couple relatively poorly between the bulb and tissue or sample, they are not appropriate to be placed in close proximity to samples, and/or they ignore or omit design considerations regarding illumination efficiency and density, and thus fail to reliably provide an improved illumination source for the performance of spectroscopy in thermally sensitive samples, such as living tissues, or in spatially constrained geometries, such as through fibers and needles.

None of the above systems suggest or teach a method and system to more efficiently deliver light to tissue or spectroscopy samples without damaging delicate samples, in order to produce a more efficient and/or high density illumination for the performance of spectroscopy in thermally sensitive samples, such as living tissues, or in spatially constrained geometries, such as through fibers and needles, such as for identifying tissue by type or state or for monitoring the oxygenation of living tissues, in vivo and in real time. A delivery-optimized, reduced heat, high-density illuminator for real-time in vivo spectroscopic applications has not been taught, nor has such a tool been successfully commercialized.

SUMMARY AND OBJECTS OF THE INVENTION

The present invention relies upon the knowledge of the design considerations needed to achieve a high efficiency delivery, high illumination-density broadband illuminator, allowing for reduced power consumption and/or heat production (these in turn facilitating deployment on or within a spectroscopic lab-on-a-chip, microdevice, or medical probe) so as to provide improved illumination for spectroscopy, with such benefits as more efficient light delivery, higher delivered intensities, reduced thermal transfer to the sample, more stable light levels, and/or allowing implementation of a light source more simply and inexpensively than has been achieved in a similar device and/or configuration using a conventional incandescent light bulb.

A salient feature of the present invention is that, while the production of broadband light is often currently associated with poor delivery efficiency of that light to a target sample, the delivered optical power can be beneficially increased through more efficient illuminator design, rather than by merely increasing the power of the light source (which also can increase heating, reduce stability, and shorten bulb life), and that those design choices include use of bulbs with integrated lenses, high conversion efficiency solid-state white or broadband LED light sources, and/or lensed optical fiber couplers in such cases where light must be transmitted by optical fiber.

Another salient feature is that, while light from a bare or reflectorized conventional bulb couples inefficiently into optical light guides or onto tissue, the effective light delivery can be improved by the use of specialized optics deployed within the light bulb or light source itself, thus allowing for a high density light delivery using optical guides such as fibers, by use of a source with a non-spherical output, or by deploying a low-heat source directly within the medical probe or device itself.

Another salient feature is that, while the production of broadband illumination is often accompanied by the production of significant unwanted heat (and that this heat frequently limits how and where a light source can be deployed), the waste heat produced for a given level of desired light incident upon the sample can be beneficially reduced by light source design choices that reduce the input power required to deliver a set amount of light power to the sample, such as more efficient coupling of a bulb to a fiber, or from the use of lower-heat light sources such as LEDs.

A final salient feature is recognition that low-heat sources frequently exhibit greater inherent optical stability than their conventional lamp counterparts, even without stabilizing feedback optics and electronics.

Accordingly, an object of the present invention is to provide an optical illuminator with an improved delivery efficiency over a conventional high-efficiency halogen projection-type bulb—that is, with an overall delivery efficiency at least twice as good, and ideally 25 times or more better, than a typically achieved by a comparable free-space coupled or fiber-coupled halogen bulb.

Another object of the invention is to provide an improved illumination density as compared to a conventional high-efficiency halogen projection-type bulb—that is, with an illumination density at least twice that, and ideally 5 times or more better, than typically achieved by a conventional bare free-space coupled or fiber-coupled halogen bulb, most preferably exceeding a continuous visible broadband power density of 10 mW/mm$^2$ for needle-based illumination for direct illumination.

Another object is to provide a white or broadband LED with sufficiently reduced local heating as to allow integration directly into small probes, devices, and even onto spectroscopy lab-on-a-chip microchips—that is, with a reduction in heat produced per mW of light delivered to the sample by at least 5-fold, and by as much as 200-fold or more, than typically achieved by a conventional bare halogen bulb either free-space coupled or fiber-coupled to a sample region.

Another object is to provide for probes and systems with integrated illuminators, delivery optics, as well as including light collection optics to collect and/or transmit light returning after interaction with the sample, while still meeting or exceeding the improvement criteria for improved illuminators as described herein.

The improved illuminator as described has multiple advantages.

One advantage is that an illuminator with sufficiently reduced heat production for a given level of target sample illumination may now be safely deployed within an instrument in proximity or in contact with sensitive samples, such as for use inside, or in contact with, living tissue, wherein use of conventional light sources would have otherwise resulted in thermal tissue injury from the light source, or required the source intensity to be reduced to such low levels that spectroscopy would have required unacceptably long integration times. In some cases, the improved illuminator may incorporate white LEDs as a light source, with as low as 20 mW of heat produced per mW of usable light delivered to the sample.

Another advantage is that bulb light sources can still be employed, but lens coupled to optical fibers rather than bare-bulb coupled to fibers, and then the bulb source can be deployed at a distance, to provide high-density light that is delivered relatively efficiently, as compared to coupling of the same bulb in the absence of transfer optics, thus requiring substantially less power to achieve a given power density at the sample. This high-density light can then be delivered to the sample using an insulating optical fiber, without the need for cooling of a high-thermal output source near the sample. The high-thermal output light source also can produce less heat due to the more efficient coupling of optical power into the fiber.

A final advantage is that high-efficiency illuminators, by virtue of their lower power consumption, can in some cases use integrated power sources, such as alkaline batteries, to allow for complete electrical separation of a probe tip from a medical system connected to the probe, despite the presence of an electrically-powered illuminator on or in the patient.

There is provided an illuminator for generating broadband light, and for delivering this light to a sample, with higher efficiency than conventional bare or fiber coupled light sources, for the purpose of enabling spectroscopic analysis. In one example, the system uses a phosphor-coated white LED and integrated collimating optics to produce continuous, broadband light from 400 nm to 700 nm in a collimated beam, which can then be transmitted through free space to a sample, such as a target tissue, resulting in a high efficiency delivery of light to the target tissue. The efficient conversion of power to light, and the high delivery efficiency, combine to allow this illuminator to remain cool during operation, further allowing it to be integrated into the tip of a medical instrument, where then broadband illuminator can illuminate living tissue. Scattered light, returning from the sample, can be collected by an optional optical output fiber, deployed within the source optics, for transfer and analysis via an optional analysis system. Medical probes and systems incorporating the improved illuminator and medical methods of use are also described.

The breadth of uses and advantages of the present invention are best understood by example, and by a detailed explanation of the workings of a constructed apparatus, now in operation and tested in model systems, animals, and humans. These and other advantages of the invention will become apparent when viewed in light of the accompanying drawings, examples, and detailed description.

DEFINITIONS

Figure 1:
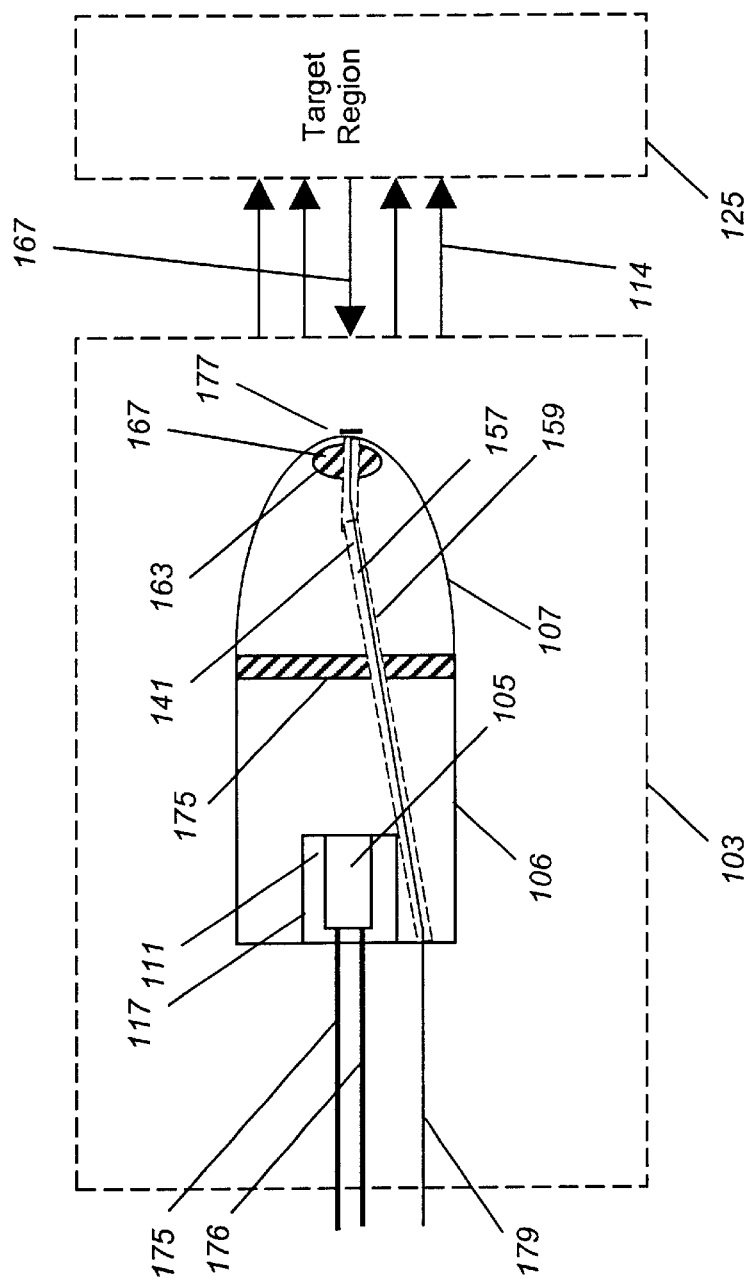
FIG. 1 is a schematic diagram of an illuminator incorporating a white LED and constructed in accordance with the invention.

For the purposes of this invention, the following definitions are provided:

Real Time: A measurement performed in a few minutes or less, and preferably in under 10 seconds. In medical or surgical use, such real-time measurements allow a procedure or a treatment plan to be modified based upon the results of the measurement.

In Vivo: A measurement performed on tissues on or within a living animal, plant, viral, or bacterial subject.

Sample: Material illuminated by a light source for spectroscopic analysis. A sample may be living tissue.

Tissue: Sample material from a living animal, plant, viral, or bacterial subject, with an emphasis on mammals, especially humans.

Target Tissue: A tissue or cell type to be detected, imaged, or studied. In the accompanying examples, one target tissue is human colonic mucosal capillary hemoglobin, while another is an ablated tumor growth.

Sample or Target Region: A physical region at which a sample or tissue to be analyzed is to be placed. The target region is the area illuminated for spectroscopic analysis.

Target Tissue Signal: An optical signal specific to the target tissue. This signal may be enhanced through use of a contrast agent. This signal may be produced by scattering, absorbance, phosphorescence, fluorescence, Raman effects, or other known spectroscopy techniques.

Scattering Sample: Material that scatters light as a significant feature of the transport of photons through the sample. Most tissues in vivo are scattering samples.

Light: Electromagnetic radiation from ultraviolet to infrared, namely with wavelengths between 10 nm and 100 microns, but especially those wavelengths between 200 nm and 2 microns, and more particularly those wavelengths between 450 and 650 nm.

Broadband or Broad Spectrum Light: Light produced over a wide range of wavelengths sufficient to perform solution of multiple simultaneous spectroscopic equations. For tissue, a width of at least 40 nm is likely to be needed, while in the preferred embodiment a broadband white LED produces light from 400 nm to beyond 700 nm.

LED: A light emitting diode.

White LED: A broadband, visible wavelength LED, often comprised of a blue LED and a broad-emitting blue-absorbing phosphor that emits over a wide range of visible wavelengths. Other phosphors can be substituted, including Lumigen™, as discussed herein. As used in the examples herein, any broadband LED could be used, even if not emitting over a full (white) spectrum. For example, an LED emitting over a range of 100 nm would be considered to be broadband.

In-Band or Usable Light: Light produced by a light source that falls into a specific range of wavelengths used in the spectroscopic analysis. This band will change, depending upon the analysis desired. For example, a bulb may have reasonable output from 380 nm to 800 microns, but only light in the 500–600 nm band may be used for one type of hemoglobin analysis, while light from 700–800 nm may be used in an analysis of tissue desaturation during thermal ablation.

Light Source: A source of illuminating photons. It may be composed of a simple light bulb, a laser, a flash lamp, an LED, a white LED, or another light source or combination of sources, or it may be a complex form including, a light emitter such as a bulb or light emitting diode, one or more filter elements, a transmission element such as an integrated optical fiber, a guidance element such as a reflective prism or internal lens, and other elements intended to enhance the optical coupling of the light from the source to the tissue or sample under study. The light may be generated using electrical input (such as with an LED), optical input (such as a fluorescent dye in a fiber responding to light), or any other source of energy, internal or external to the source. The light source may be continuously on, pulsed, or even analyzed as time-, frequency-, or spatially-resolved. The light emitter may consist of a single or multiple light emitting elements, such as a combination of different light emitting diodes to produce a spectrum of light.

Conventional Light Source: The typical broadband illuminator light source cited in the art and/or used in commercial systems is a bulb lamp, such as high-efficiency halogen lamp or arc lamp.

Luminous Flux: The total optical power output of a light source over a given spherical angle, usually expressed in Lumens (lm), but intraconvertible with watts or photons per second.

Luminous Efficiency: The power output of a light source in the desired wavelength range for a given amount of supplied input power, in Lumens of output per Watt of supplied power (Lm/W).

Conversion Efficiency: As used herein, similar to Luminous Efficiency but expressed as the fraction of input power effectively converted to illumination of the desired waveband. For visible light, a luminous efficiency of 242.5 lumens per watt would represent a conversion efficiency of 100%. Typical conversion efficiencies for incandescent bulbs to visible light are 4–14%, while LEDs can have in-band efficiencies from 10% to well over 40% (about 100 Lm/W) for newer white LEDs.

Transfer or Coupling Efficiency: As used herein, the percentage of the total usable light output of a light source that is effectively delivered to a finite sample or into a transmission fiber for delivery to a sample.

Delivery Efficiency: The fraction or percent of input power to a light source that eventually reaches a target tissue as illumination in the desired wavelength band. This is a function of both source and coupling optics, as well as reflects the size of the measured target area itself. Also equal to the conversion efficiency multiplied by the transfer efficiency.

Optical Density: As used herein, the optical power of usable wavelengths incident upon a target region per unit area, in $mW/mm^2$.

Thermal Load: As used herein, the amount of heat produced for a given amount of usable delivered optical power, in mW heat per mW delivered light. This factor indicates how hot a given illuminator will run during operation in order to deliver a set amount of illumination required. The lower this value, the cooler the illuminator will run to achieve a set amount of delivered illumination of the target sample.

Transferable Thermal Load: As used herein, similar to thermal load above, but restricted to the heat at risk for transfer to the sample, in mW heat transferable to the target region per mW delivered light to the target region. The lower this value, the cooler the sample will be when achieving a set amount of delivered illumination. Thus, if a given illuminator is fiber coupled and is physically separated from the spectroscopy sample, the transferable thermal load is zero, even if the source runs hot, as the heat does not reach nor affect the spectroscopy sample; however, if the illuminator is near the sample, such as in the tip or handle of a medical probe, then part or all of this heat is at risk for transfer to the sample, and the transferable thermal load is equal to part or all of the thermal load.

Negligible Transferable Thermal Load: As used herein, a transferable thermal load of less than 1 mW per mW of delivered light is considered negligible.

Light Detector: A detector that generates a measurable signal in response to the light incident on the detector.

Optical Coupling: The arrangement of two optical elements such that light exiting the first element interacts, at least in part, with the second optical element. This may be free-space (unaided) transmission through air or space, or may require use of intervening optical elements such as lenses, filters, fused fiber expanders, collimators, concentrators, collectors, optical fibers, prisms, mirrors, or mirrored surfaces. For most optical elements, there is an entry end, where light enters, and an exit end, where light exits. This can also be defined as a proximal end nearest the light source, and a distal end nearest the sample. These two descriptions are not equivalent, for example the proximal end of an optical fiber may be the entry or the exit end, depending on whether light in the fiber is traveling toward or away from a sample region.

Description of a Preferred Embodiment

One embodiment of the illumination device will now be described. With reference to FIG. 1, the illuminating device or illuminator 103 is illustrated with its component parts. Broad spectrum white light is emitted by a high conversion-efficiency white LED source 105 (in this case, The LED Light, model T1-3/4-20W-a, Fallon, Nev.). Diode source 105 is embedded into plastic beam-shaping mount 106 having shaped lens end 107. The plastic is an optically clear epoxy 111 to allow light generated in well 117, emitted over a 20 degree half angle by the diode source 105, to be collimated, thus remaining at a near-constant diameter after passing through lens 107. Light then is able to pass forward, in a collimated beam as shown by light path vectors 114, with some to reach and be optically coupled to target region 125 (not a part of illuminator 103).

A portion of the light reaching target 125 is scattered and reflected, and returns as returning scattered and reflected light 128 to collection fiber 141. Collection fiber 141 is a black-coated optical fiber and is shielded from stray light from source 105 within the body of illuminator 103 by this black coating (not shown). Fiber 141 is in turn secured by optical clear epoxy 157 within channel 159. Fiber 141 is additionally shielded from stray light at the surface of lens 107 by shallow well 163, which is filled with light-absorbing black epoxy 167.

Illuminator 103 has two electrical connections 175 and 176, and one optical connection, namely fiber connection 179, the non-patient, or monitor end, of collection fiber 141. Electrical connections 175 and 176 are used to provide power to diode 105, while connection 179 to optical fiber 141 is used to collect returning light 128, reflected or scattered from target 125, and returning to fiber 141 at the target or patient end of illuminator 103.

Optionally, polarizing filters 175 and 177 can be placed in parallel or with crossed-axes, in order to select or exclude specularly reflected light, respectively, based upon retention or loss of polarization.

Figure 2:
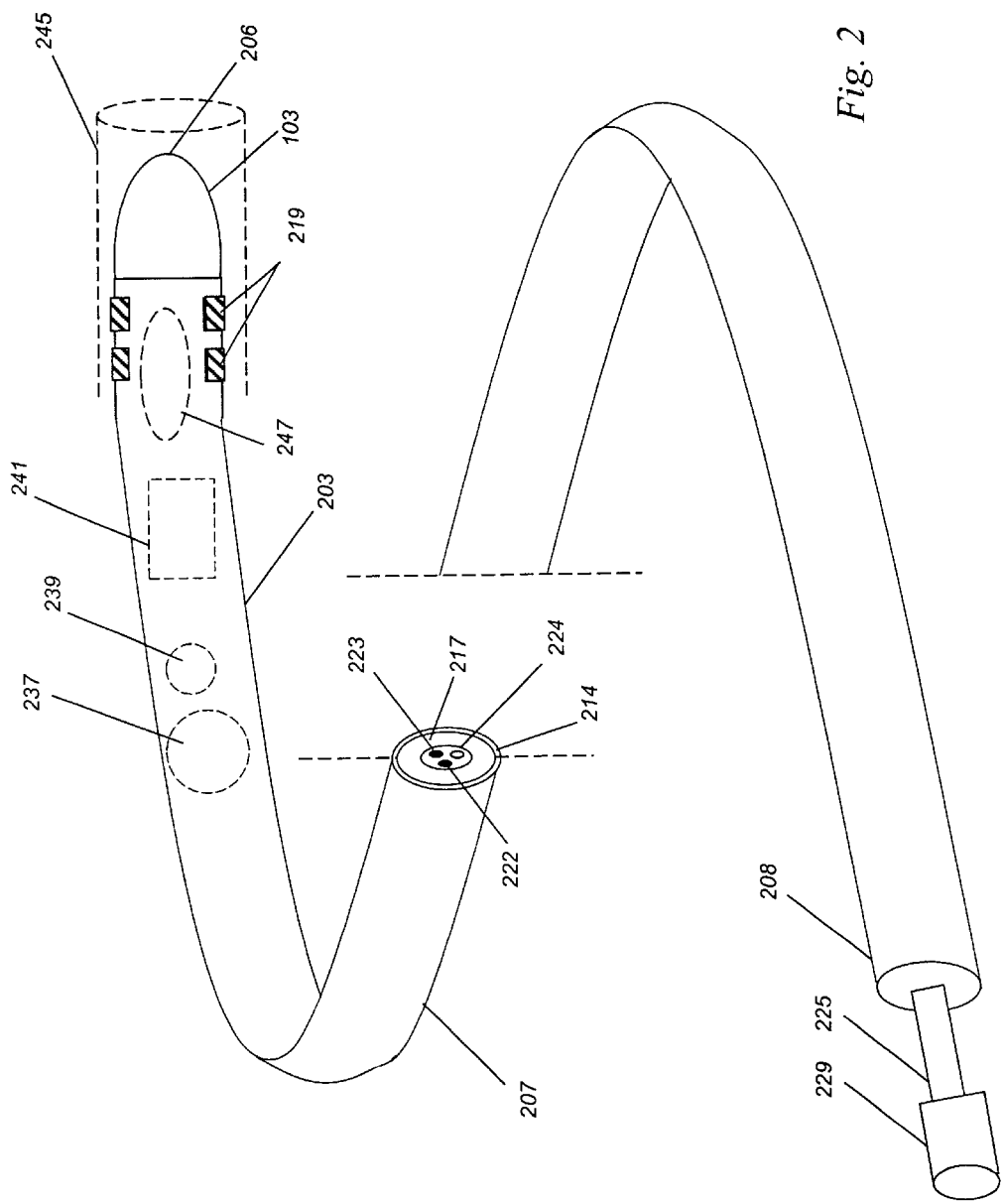
FIG. 2 shows the improved illuminator of FIG. 1 as incorporated into a medical catheter.

Illuminator 103 can optionally be embedded within a medical device, as shown with illuminator 103 embedded in medical catheter probe 203 (FIG. 2). Probe 203 has patient-end 206, catheter body 207, and monitor-end 208. In probe 203, flexible probe body 207 consists of a section of US FDA class VI heat shrinkable tubing 214 surrounding medical grade Tygon™ tubing 217, both of which are further swaged to light illuminator 103 at swage points 219 near probe patient end 206. Wires 222 and 223, from electrical connections 175 and 176 of source 105 of illuminator 103 (as shown FIG. 1) travel through concentric tubes 214 and 217, into extension tubing 225, and terminate in plug 229 at patient-end 208. Optical connection fiber 224, from optical connection 179 of source 105 of illuminator 103 (as shown FIG. 1) travels from the patient tip of probe 203, running parallel with wires 175 and 176 inside concentric tubes 214 and 217, to terminate in monitor-end plug 229. Plug 229 is a reversible connector plug containing electrical connections, optical connections, or a hybrid mix of both.

Optionally, it may be beneficial (such as less costly) to separate the optical and electrical terminations of plug 229 into two plugs, one plug containing only optical connections and the other plug containing only electrical connections.

Another option is that, in lieu of electrical connections for powering source 105, which leave probe 203 at plug 229, wires 175 and 176 may terminate at an internal power source, in this example button battery 237, which can be fully incorporated into the medical probe, providing power to illuminator 103 upon switching of click-on/click-off switch 239, also incorporated into the body of the probe. In this case, the source power electrical connections at plug 229 may be able to be eliminated from the plug.

Probe 203 may be "smart" "with optional, chip 241 integrated into probe body 207. This chip may retains information useful in the operation of the device, such as calibration parameters, a reference database, a library of characteristic discriminant features from previously identified tissues, and so on, and this information may be accessible via plug 229. Additionally, information on chip 241 may include probe identification, probe serial number, use history, calibration details, or other information accessible through plug 229.

Next, again optionally, if light leaks, or is allowed to leak, from an integrated illumination source, this can create a glow in body 207 of probe 203 at catheter location 247. If a logo, or other image, is placed on probe 203 at point 247, the logo will now glow in a darkened room, which is an appealing effect.

Figure 3:
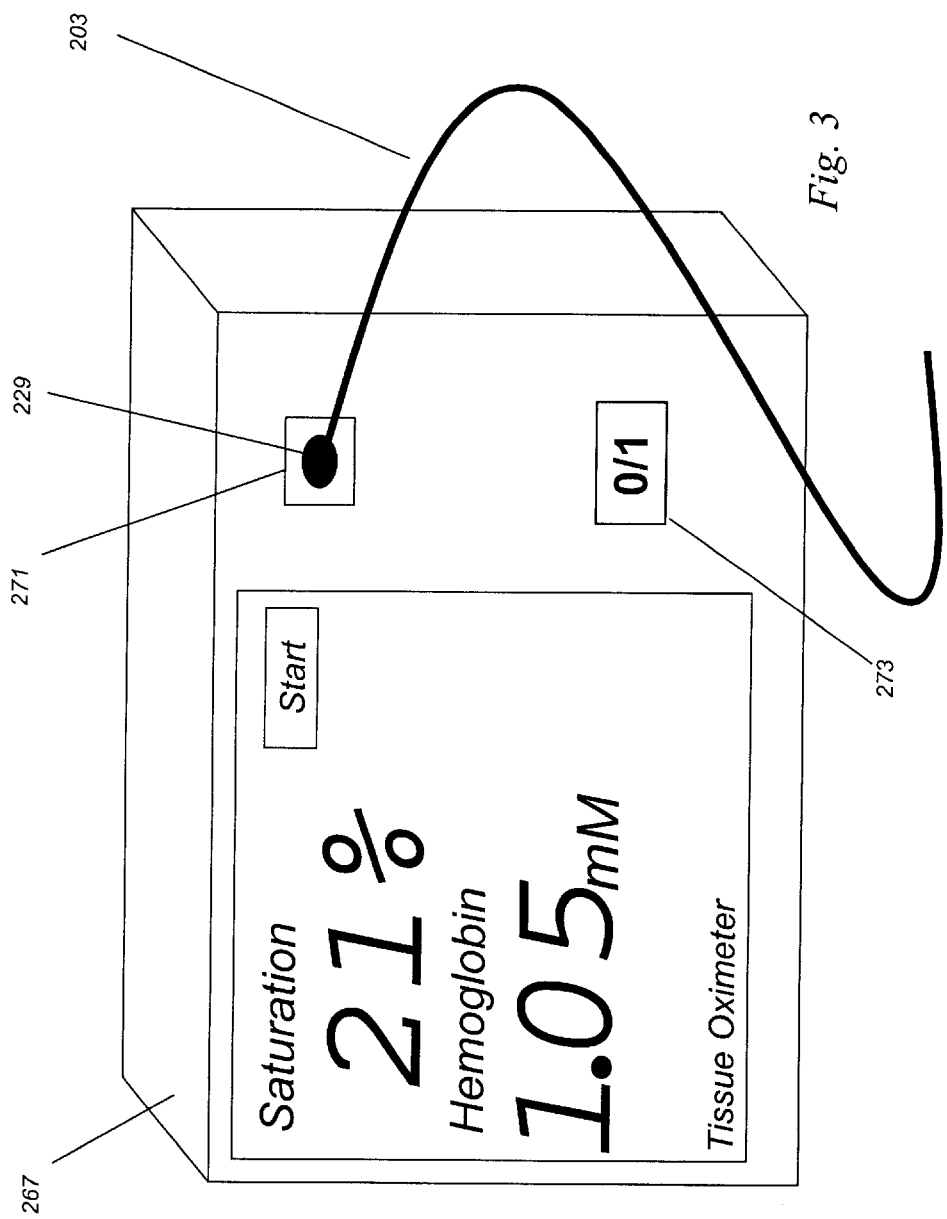
FIG. 3 is a drawing of a medical monitor to which the probe of FIG. 2 is attached to form a complete medical system.

Last, as noted, illuminator 103 may be incorporated into a medical device, such as probe 203 as shown in FIG. 2, or it may be incorporated into a medical system, such as medical system 267 as shown in FIG. 3 with probe 203 attached to system 267 via socket 271. An example of such a spectroscopic monitoring system is disclosed in U.S. Pat. No. 5,987,346. An example of illuminator 103 incorporated into a battery-operated system for field use is a portable spectrophotometer for water analysis. In such a case, illuminator 103 may shine directly on the sample, making both battery life and thermal transfer significant issues; an example of an invasive medical source would be if illuminator 103 were incorporated into a medical probe, needle, or catheter, which is then used internally within the body, such as in the gastrointestinal tract or in a coronary blood vessel. If illuminator 103 remains too warm for direct tissue contact, then illuminator 103 may be placed in the body of the medical probe (such as within the cable) but outside of the patient, or illuminator 103 may be moved into the case of monitor 267 itself. In such instances, it may be essential to have a means to stabilize the fiber with respect to light source 105 of illuminator 103, such as plug 229 and socket 271.

Operation of the device may now be described.

In this example, illuminator 103 is incorporated into medical catheter probe 203, and connected via plug 229 to spectroscopic monitoring device 267 via socket 271, as shown in FIG. 3. Power to probe 203 is provided by monitor 267, which internally induces source 105 of illuminator 103 to generate light. Initially, patient end 206 of probe 203 is covered with standardization cap 245. When spectroscopic monitor 267 is switched on using power switch 273, an internal reference spectrum (not shown, but fully disclosed elsewhere, i.e., in U.S. Pat. No. 5,987,346) is collected with standardization cap 245 in place. Next, cap 245 is removed, the probe is placed in contact with tissue, and light from illuminator 103, embedded in probe 203, reaches target region 125, in this case, living human tissue. Collimated light 114 arriving at target region 125 is scattered and/or reflected, and some portion of returning scattered and reflected light 128 light is collected at the distal, patient end of collection fiber 141 and returned to monitor system 267 via the proximal, monitor end of exit fiber 179 of illuminator 103.

Figure 4:
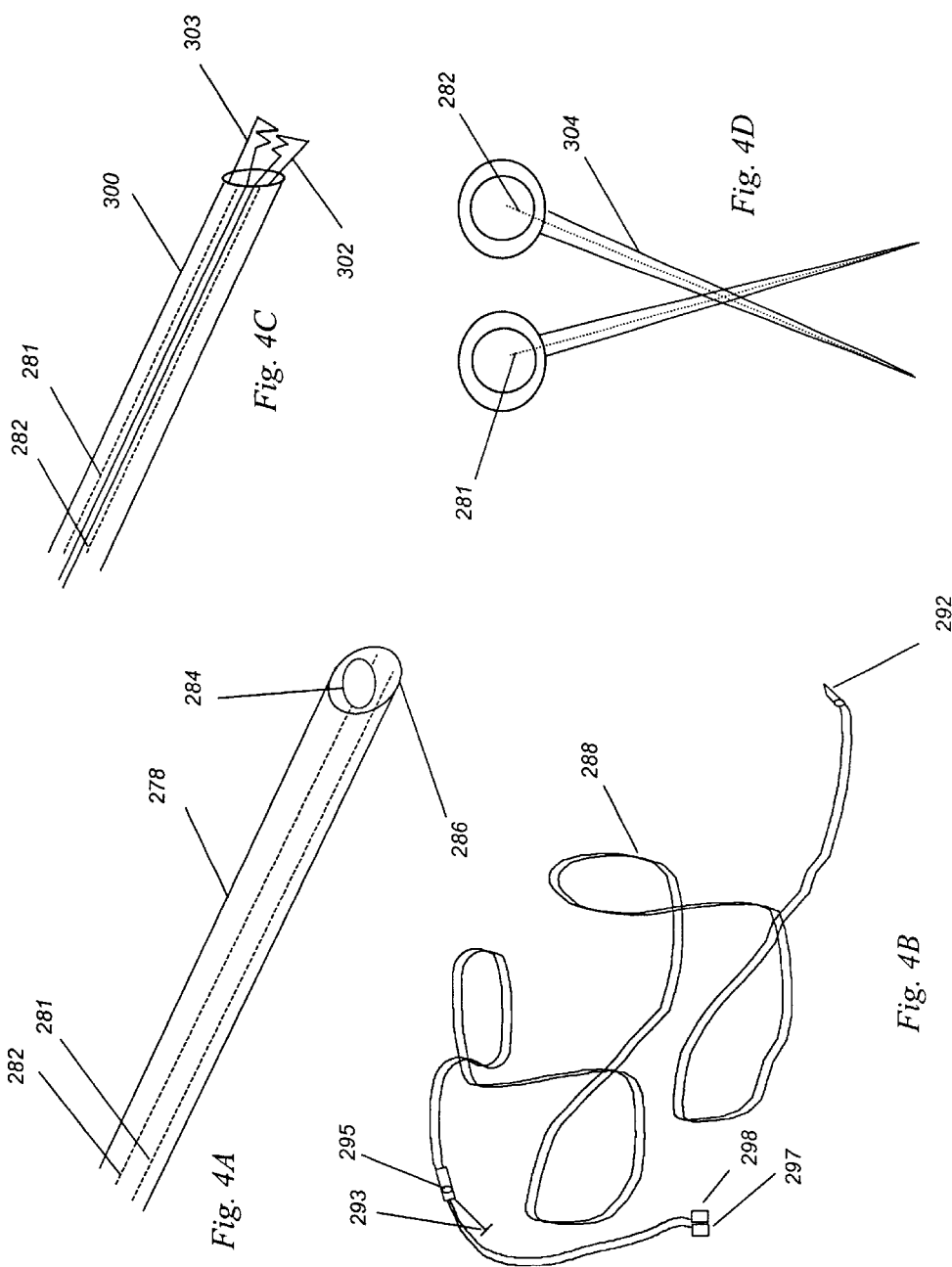
FIGS. 4A–4D show additional medical probes incorporating the improved illuminator.
Figure 6:
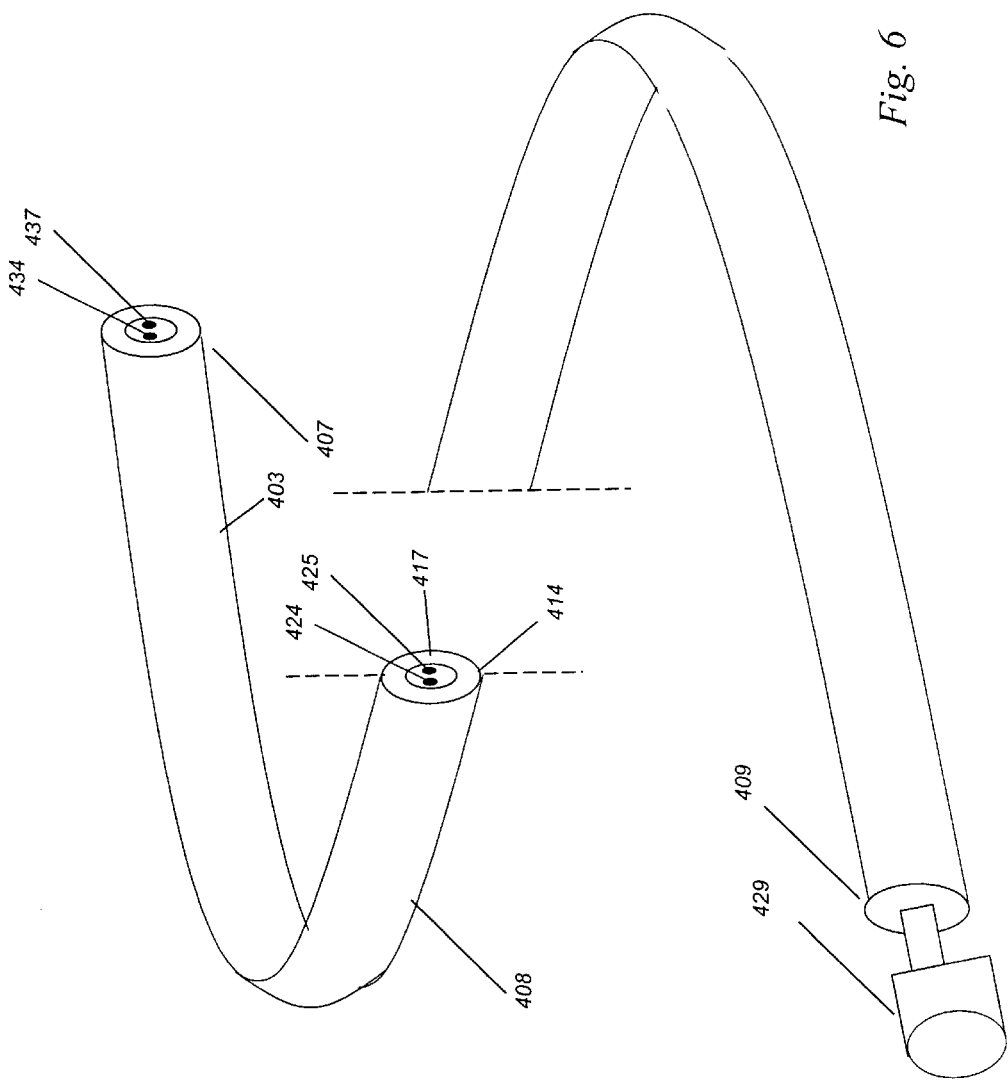
FIG. 6 shows the improved illuminator of FIG. 5 as incorporated into a medical catheter.

Examples of optical probes are shown in FIGS. 2, 4A–4D, and 6. FIGS. 2 and 6 show probes best suited to medical endoscopic use, as previously described. FIGS. 4A–4D show other types of medical illuminator probes, such as a targetable injection needle 278 with illumination coupling optical fiber 281, light collection optical fiber 282, injection port 284, and cutting edge 286, as shown in FIG. 4A. FIG. 4B shows catheter 288 with extendable needle 292 controlled by plunger 293, syringe attachment port 295 for injection through catheter 288 to needle injection port 295, and with illumination fiber 281 and collection fiber 282 embedded internally (not shown) into needle 292 in a manner similar to that shown for needle 278, FIG. 4A, with illumination fiber 281 connected to plug 297, and detector fiber 282 connected to plug 298, as shown in FIG. 4B. FIG. 4C shows nibbler 300 with illumination fiber 281 and collection fiber 282 embedded into jaws 302 and 303, respectively, for simultaneously monitoring and removing tissue. Lastly, scissors 304, FIG. 4D, with illumination fiber 281 and collection fiber 282 embedded into the body of scissors 304. The tools shown in FIGS. 4A–4D are intended to be illustrative of the breadth of potential illuminator probes. Incorporation of the illuminator of the present invention into other medical or surgical instruments, spectroscopic and laboratory probes, and the like, can easily be accomplished by one skilled in the art, and no undue limitation is intended or implied by omission of other examples.

Of note, when light from a noninvasive or invasive system penetrates into tissue, the photons traveling between the light source and the light detector take a wide range of paths. The present device takes advantage of this effect as the scattering provides an averaging and volume sampling function. When detected illumination is measured after it has propagated through the tissue over substantially non-parallel multiple courses taken through the tissue between the time the photons are emitted and then detected, many regions of the tissue can be sampled, not merely the tissue on a narrow line between emission and detection. This allows a small but important feature, such as a the ability to sample the subsurface capillary layer of gastrointestinal mucosa, even if the probe itself is placed 1 cm from the intestinal wall.

In this embodiment, light source 105 of illuminator 103 receives its power from electrical inputs 175 and 176. Here, source 105 is a white LED, source 105 just as easily be any broadband LED, or be a polymer plastic that emits light under the influence of electrical power, or be a laser with broadening of the waveband via the input fiber impregnated with fluorescent dye, and so on, provided that source 105 meets the technical requirements of the improved illuminator disclosed herein. As is noted in the latter example, non-electrical types of input are possible—for example, source 105 may be a mixture of fluorescent polymers embedded in plastic, and source 105 is activated by supplying external light to the source, rather than by applying power.

Also, as noted earlier, an integrated battery or set of batteries can provide power from within the device, reducing cost of the connection tip. An added advantage of this battery-based approach is that it removes the need for electrical connection to the illuminator, as an added safety feature.

Figure 5:
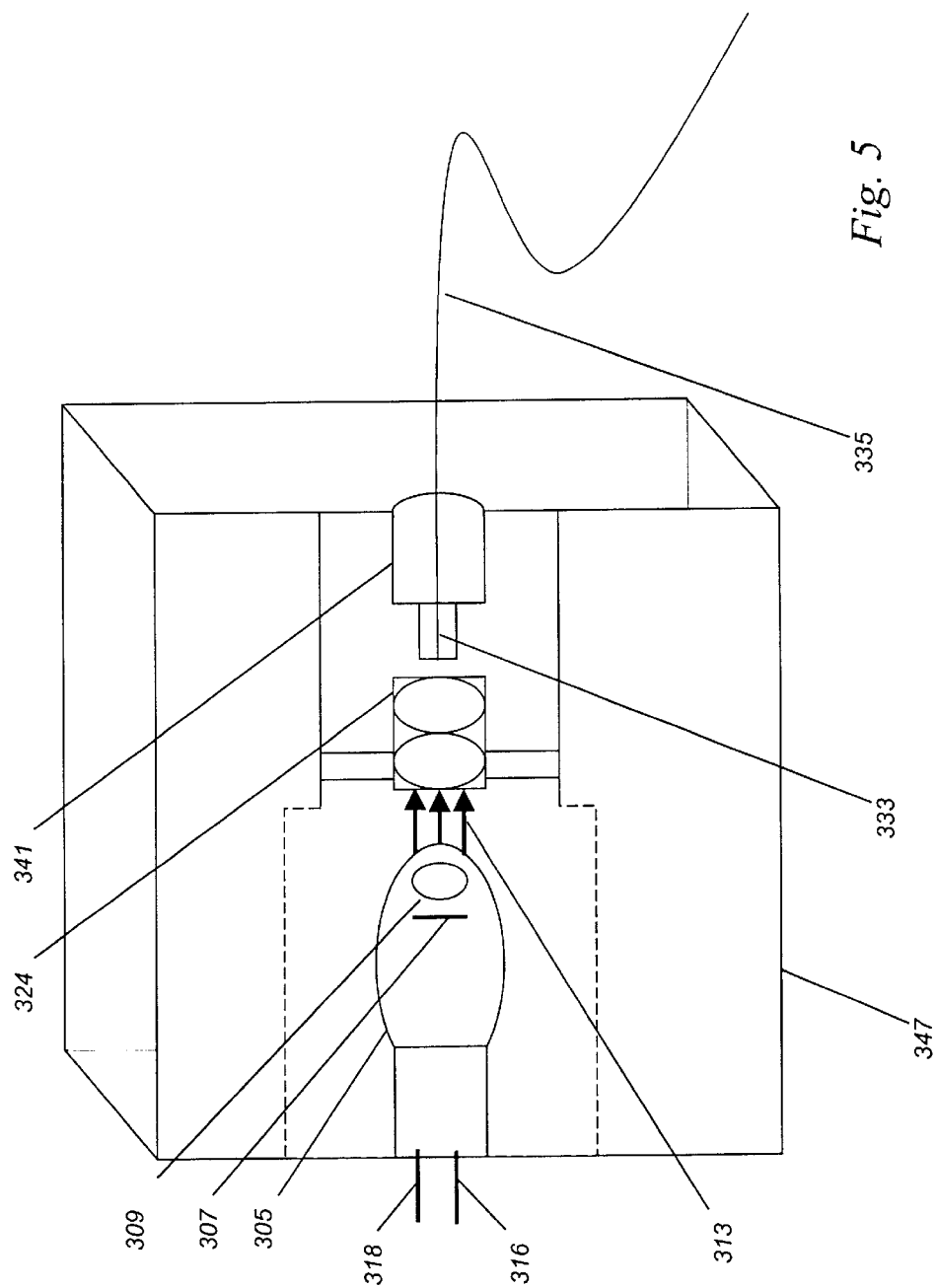
FIG. 5 is a schematic diagram of an illuminator incorporating an internally-lensed halogen bulb and constructed in accordance with the invention.

Illuminator 103 can still be an incandescent bulb, in certain cases, again provided that source 105 still meets the technical requirements of the improved illuminator disclosed herein. Integrated lenses in light bulbs allow for a far greater capture of light, improving the efficiency of the bulb and yielding high photon densities at the exit of the fiber. In this manner, a 15 W bulb can be used to supply power equal to, or more than, that of a 125 W projector bulb. FIG. 5 is an example of this type of bulb-based illuminator. White light bulb 305 with filament 307 near integrated lens 309 produces collimated beam 313. In this embodiment, bulb 305 receives its power from electrical inputs 316 and 318. Collimated beam 313 is then refocused by reversed beam expander 324 onto entry 333 of fiber 335, with fiber 335 held stable and aligned in detachable fiber holder 341, all held together in supporting socket and block 347.

Since the illuminator of FIG. 5 operates at a high temperature, the illuminator would be deployed in medical monitor 267 away from the patient. In this case, block 347 is a heat-conductive metal to allow for heat sinking of block 347 to the frame of monitor 267.

Medical probes that connect to this illuminator would not require integrated light sources, rather they would couple light from a bulb-based illuminator, such as the illuminator shown in FIG. 5, to the target region using optical fibers. In FIG. 6, a medical probe modified to removably connect to the optical illuminator of FIG. 5 is shown. As noted, medical catheter 403 no longer contains an integrated illumination system. Probe 403 has patient-end 407, catheter body 408, and monitor-and-illumination-end 409. In probe 403, flexible probe body 408 consists of a section of US FDA class VI heat shrinkable tubing 414 surrounding medical grade Tygon™ tubing 417. Optical illumination fiber 424 and optical collection fiber 425, travel from patient tip 407 of catheter probe 403, running through catheter body 408 inside concentric tubes 414 and 417, to terminate at plug 429 of monitor end 409. Plug 429 is a reversible connector plug containing electrical connections, optical connections, or a hybrid mix of both (in this case, only optical connections are present).

At patient end 407 of catheter 403, optical illumination fiber 424 emits light toward a target region. Light reaching sample tissue in this region, is scattered, absorbed, rotated, re-emitted, and interacted with in multiple ways. A portion of this light returns to optical collection fiber 425, where it is transmitted to medical monitor 267, for processing and analysis, via plug 429 connecting to socket 271 of monitor system 267.

Catheter 403 has several advantages over catheter 203. First, there are no electrical connections to the patient required, reducing the risk of electrical injury, such as burns or myocardial fibrillation. Another advantage is that the catheter diameter can be much smaller that can be achieved with an integrated illuminator, as optical fibers may measure only 100 microns in diameter, while light sources measure a millimeter to several centimeters in width.

EXAMPLES

The breadth of uses of the present invention is best understood by example, seven of which are provided below. These examples are by no means intended to be inclusive of all uses and applications of the apparatus, merely to serve as case studies by which a person, skilled in the art, can better appreciate the methods of utilizing, and the scope of, such a device.

Example 1

Improved Delivery Via Improved Conversion Efficiency

One method to improve effective delivery efficiency is to improve the conversion efficiency—that is, to reduce the amount of power needed to produce a given amount of usable light.

In order to evaluate the impact of design considerations, we modeled the expected improvement in the efficiency of light delivery achieved by altering various aspects of an illumination source design, and then verified our model data using experiments. This model incorporated known features of light generation from tungsten fiber lamps with and without halogen recycle, the transmission characteristics of certain optical fibers, known general characteristics of broadband light emitting diodes (LEDs), and each aspect of the model was tested in the laboratory to confirm agreement of the predictions to those of measured results.

First, we considered a high efficiency halogen light bulb free-space coupled to a tissue sample—that is, illuminated in air and without intervening optics. When operating at halogen lamp temperatures (3650 K filament, 120–140° C. bulb), a good lamp will configured ideally produces 14 Lm/W. For this modeling, we assume that the bulb filament is infinitesimally small, such that the intensity of the light over any sample is given by the bulb's light output times the fraction of a sphere (with a center at the filament and a surface at the sample) that is intercepted by the sample. The highest theoretical limit for light delivery to a sample would be either placing the filament against the sample. Of course, doing so would damage many types of samples, and one object of this invention is to increase the delivery efficiency of light while maintaining reduced or safe thermal transfer to the sample. Therefore we have assumed a lamp to tissue distance of 50 mm as a minimum, in order to allow for thermal shielding and heat sinking, with the lamp illuminating a 10 mm diameter circular target area.

Using calculations similar to those presented in the background section, a 15 W lamp halogen lamp is now modeled. In practice, increasing the wattage of the lamp increases the heat output of the bulb, and thus increases the distance the bulb needs to be from the sample, in order to protect the sample, and therefore does not result in better illumination of the sample. At a conversion efficiency of 14% for halogen projection lamps at 3600 K, 12.9 W is lost as heat while 2.1 W is converted to usable light. A large circular target, measuring 10 mm in diameter, is considered, which intercepts light over an area of 79 mm$^2$ (assuming a flat target). This intercept area is taken from a total emission over a sphere, with the center at the filament and the surface at the target 50 mm from the filament (due to distance kept due to the heat produced), measures 2,618 mm$^2$, for a free-space transfer efficiency of 3.0%. Combined with the halogen conversion efficiency, this results in a net delivery efficiency of 0.4%, with 63 mW delivered to the sample and with 205 mW of heat produced for each mW of visible light delivered to the target. The intensity of visible light falling on the circular target sample is 0.80 mW/mm$^2$. However, because of the high heat production and surface temperatures exceeding 120° C. such a bulb is difficult to integrate directly into an invasive probe or catheter, or deploy on a solid-state device such as in integrated circuit, nor is a 5 cm illumination distance always achievable, such as when a catheter is placed inside the body or when an illuminator is deployed on an integrated circuit.

Next, we considered alternative sources of broadband light with more efficient conversion of energy to light, for example, phosphor-based broadband LEDs known as a white LEDs. As a device group, LEDs are, in general, more efficient converters for several reasons, as follows:

First, LEDs, including white LEDs, produce light more efficiently than halogen bulbs. The conversion efficiency of an LED can run higher than 50%, but typically run 25–40%, which is 2 to 3 times the efficiency of a good halogen bulb.

Second, LED's, again including white LEDs, tend to emit light concentrated into a narrower range of wavelengths than bulbs, and thus they produce more usable in-band light, with less wastage outside of that range, and therefore tend to be more effectively brighter than for a halogen bulb operating with the same total light output.

Third, an important feature of LEDs in general, including many white LEDs and laser LEDs, is that they can emit light over a narrower range of spatial angles (e.g., non-uniform non-spherical output). Thus, the light that is produced may be more concentrated in space, and therefore more usable for spectroscopy, than a conventional bulb.

Fourth and last, recall that an improvement in efficiency allows less energy to be used, which results in less heat, allowing the LED to be moved closer to the sample, and so on, with an exponential reduction in heat and effective illumination produced.

The net effect of this improvement in conversion efficiency is that it allows closer placement of the light source to the sample, and this can be seen by repeating the above calculations for a white LED.

For comparison to the halogen bulb, consider a white LED with a current of 50 mA with a 3 V drop across the diode, for a power consumption of 150 mW. As an LED has no requirement for the high bulb temperatures required by halogen recycle, the surface of the LED package can remain cool to warm to the touch. This low temperature allows the LED to be brought nearly in contact with the sample, if needed, delivering even higher light levels and allowing for further power reductions. For this example, we assume that the LED-based illuminator at the same 50 mm distance from the sample used for the halogen bulb calculations earlier in this example.

The power consumed by the LED in this example, 150 mW, is 100 times less power required for the 15 W projection bulb discussed above. White LEDs can reach efficiencies of 40% or more, but for this example we assume an efficiency of 25%. At this efficiency, the white LED emits 63 mW of light while producing 188 mW of heat. Because LEDs emit over a narrow angle, the size of the emitting surface can be small, and LEDs often have their plastic packaging formed in the shape of a collimating lens very near the emission source, a large degree of the LEDs light can be captured and projected into a narrow collimated beam. In theory, the majority or all of the emitted light may be captured and transferred from a white LED with a forward-directed reflectorized hemispheric illumination chamber and collimation optics, while in practice this number is likely to be 10–50% or less unless a laser diode is used. For this example, we estimate a transfer efficiency of nearly 20%, for a net delivery efficiency of 4–5%. This net delivery efficiency is over 10 times higher than the comparable projection bulb at the same 50 mm distance.

As a result, the white LED delivers 7 mW of usable light to the sample area—over 10% of the light level as the 63 mW delivered by a bare 15 W projection bulb at 5 cm distance, but with only 16 mW heat produced per mW of light delivered to the tissue, rather than 205 mW heat produced by the halogen bulb per mW of light delivered. Use of the White LED therefore results in an 11-fold improvement in delivery efficiency and a 114-fold reduction in heat produced to achieve comparable illumination levels at the tissue target. This allows direct embedding of a white LED illumination source into medical catheters and probes, and placement of a white LED directly onto lab-on-a-chip configurations.

For free-space illumination, these results are summarized in the table below:

TABLE 1

Broadband Free-Space Coupling for Halogen Bulb vs. White LED.

| Type of Illuminator Source | Conversion Efficiency (%) | Coupling Efficiency (%) | Delivery Efficiency (%) | 1 cm Field Intensity (mW) | Transferable Thermal Load (mW heat per mW Delivered Light) |
|---|---|---|---|---|---|
| Conventional Bulb | 4% | 3% | 0.12% | 18.0 | 800 mW |
| Halogen Bulb | 14% | 3% | 0.42% | 63.0 | 205 mW |
| White LED | 25% | 19% | 4.69% | 7.0 | 16 mW |
| Improvement of White LED over Halogen in Probe | 1.8× | 6.2× | 11× | 0.11× | 12.8× |

In the example in Table 1, the bulb and LED sources are placed at 50 mm distance from the sample due to heat production; though for the low heat production from the LEDs would allow them to be placed much closer, even down to several millimeters from the sample, which would result in reduced transfer losses and lead to further improvement in net delivery efficiency. In fact, when brought within 1 mm of a sample, the white LED has a measured light density over 15 times greater than that of a halogen bulb at 5 cm, but without the limitations on source and sample separation due to heat produced.

The performance of a white LED can be even better than the above discussion suggests. A white LED is a relatively narrow-spectrum broadband emitter, unlike a conventional bulb which radiates over a wide range of wavelengths. If only a narrow portion of the spectrum is required, the efficiencies of Table 1 above are amplified. For instance, consider a hemoglobin analysis that requires only the wavelengths of 500–600 nm. In this case, the usable light from a bulb sources is not the sum total of the visible light produced with 14% conversion efficiency, but rather only a narrow waveband of this light produced with only 2.8% efficiency in the halogen lamp. This reduces the net in-band delivery efficiency to 0.08%, making the LED substantially better in light density and heat produced per mW usable light. In this case, for a hemoglobin analysis which requires only 500–600 nm light, a white in-band LED is 56-fold as delivery efficient as a conventional bulb, with a 64-fold reduction in heat produced at the probe for every mW of in-band light generated, as shown in Table 2, below:

TABLE 2

In-Band Free-Space Coupling For Halogen Bulb vs. White LED.

| Type of Illuminator Source | Conversion Efficiency (In-Band %) | Coupling Efficiency (%) | Delivery Efficiency (%) | 1 cm Field Intensity (mW) | Trans. Thermal Load (Heat Delivered per mW Light Delivered) |
|---|---|---|---|---|---|
| Halogen Bulb | 2.8% | 3% | 0.08% | 12.6 | 1010 mW |
| White LED | 25% | 19% | 4.69% | 7.0 | 16 mW |
| Improvement Using White LED | 8.9× | 6.3× | 56× | 0.56× | 64× |

Use of a white LED has several specific advantages. A first advantage is that cool, high-delivery sources such as diodes and plastic coupling optics are sufficiently inexpensive so as to make the device disposable, resulting in a reduction in risk of infection or drift during resterilization. Also, the cost of many meters of coated optical fiber for coupling an illuminator to a medical probe may exceed the cost of white LEDs, even without fiber termination and polishing costs considered, and thus switching to an embedded white LED can lead to cost savings.

Another advantage is that the diode illumination source may be rapidly switched on and off, providing the ability to obtain real-time estimates of background illumination.

Another advantage is diodes tend to be more stable light sources than incandescent lamps, reducing drift in the source intensity, and allowing for calibration at the factory rather than in the field. This elimination of calibration and/or stabilization during use can greatly simply use of a medical probe containing an embedded white LED. Further, an LED may be placed into a disposable or reusable probe with the realistic explanation that bulb failure is highly unlikely.

Another advantage is the relative coolness of the white LED may allow improved spectroscopic light sources to be produced with sufficiently low heat production that they can be safely deployed within a probe itself, such as within a spectroscopically-enabled medical instrument or upon a self-contained laboratory-on-a-chip.

Use of a white LED is novel for medical probe or for an on-chip spectroscopy purposes, and has not been previously disclosed, and the degree of the improvement in transfer efficiency is unexpected from casual considerations.

Example 2

Measurement Using LED and Bulb-Based Probes

In order to test the validity of the data generated using the model shown in Example 1, we constructed two working probe types, one set using a halogen bulb and a second set using a white LED. Light incident on a tissue phantom was then measured using a silicon-based photodiode system (EXFO, model FOT-50, Quebec, Canada).

In these measurements, the skin was illuminated using the 15 W halogen bulb and the 250 mW white light LED described in the preferred embodiment. Light returning from the skin was collected using a 3.5 mm diameter circular aperture and measured in overall intensity from 400 nm to 1100 nm.

Results for in-band free-space illumination are shown in Table 3, below:

TABLE 3

Measured Broadband Free-Space Coupling For Bulb vs. White LED.

| Type of Illuminator Source | Current (mA) | Voltage (V) | Power (mW) | 1 cm Field Intensity (mW) | Max Bulb Temp (° C.) | Trans. Thermal Load (mW Heat/Light/ cm$^2$) |
|---|---|---|---|---|---|---|
| Halogen Bulb | 1120 | 8.2 | 9180 | 1.66 | 143 | 4756 |
| White LED | 50 | 3.4 | 170 | 0.71 | 31 | 180 |
| Improvement of White LED over Halogen | | | 54× | 0.42× | | 26× |

The 26-fold reduction in transferable thermal load is, within experimental error, in agreement with the projected improvement of 64-fold. The relative low power delivered to the field for both the halogen and the white LED (10–15% of projected values in Table 2), suggest losses not accounted for (such as surface reflections and other losses), or poor coupling of the light into the optical power meter. The central result is not affect, however, as the relative improvements seen remain accurate.

Importantly, we have achieved a central goal of the improved illumination source: improved delivery efficiency with sufficient reduction in power required that the device could operate internally in the body, or in contact with living tissue. In the above study, the decrease in operating power for the LED was a 54-fold reduction in power, as compared when using the halogen bulb. This reduction was due to improved conversion of power to usable light, as well as due to the reduced spatial emissions of the white LED device due to the integrated cup and lens. As a result, the transferable thermal load is also greatly reduced. In this example, the operating temperature of the LED probe was 31° C., in a 21° C. room, which is well below the temperature of the human body (37° C.). In contrast, the halogen bulb operated at a temperature sufficiently high to boil water, and were the halogen bulb to operate even 70 degrees cooler, it would still be sufficiently hot to fry an egg. Thus, the LED, though improved conversion of power to usable light, has allowed construction of a biologically-safe probe, whereas use of the halogen bulb in tissue could be dangerous.

Example 3

Improved Delivery Via Improved Transfer Efficiency

An alternative method for improving the net efficiency of light delivery is to improve the coupling of the light source to the sample, measured by transfer efficiency.

For this example, we considered again a bright halogen projection-type bulb, too hot to put directly next to a sample such as tissue, and in this case even too hot to be safely placed into the handle or tip of a device such as a medical probe.

One way to get around the heat issue is to fiber-couple the bulb to the sample, thus removing the inefficient and hot light emitter from the vicinity of the sample. As the conversion efficiency of a high-efficiency halogen bulb is difficult to modify, improving the delivery efficiency represents an approachable way for increasing the net transfer efficiency.

As noted, the best coupling of light would occur in theory if the fiber could be placed in contact with the filament itself, as this is where the sphere of light from the filament is smallest and where the surface of that sphere has the highest power density. While this cannot be achieved in practice, as the fiber would melt, the fiber can be optically coupled to the filament in effectively the same manner, with a reduced risk of melting, by using lenses, mirrors, or other optical focusing and transmission devices. Certain constraints apply, such as light cannot be concentrated to a higher density than exists at the filament using such lenses and mirrors (an exception to this are NIOCs, non-imaging optical collimators, but the wide angles of photons exiting these NIOC devices can make concentration of photons difficult in some cases), but power densities near the filament power density limit can be approximated if the majority of the bulb power is redirected using a reflector (e.g., posteriorly) and/or lens (e.g., anteriorly).

In practice, a lens outside the bulb must be large, in order to capture a significant fraction of the photons leaving the filament. As an alternative, a lens can easily be integrated into the bulb or bulb glass, capturing a wide angle of forward-directed photons and collimating or focusing these photons. We model a two-lens system in which a lens is integrated into the bulb housing only 2 mm from the filament, thus collimating and capturing many of the forward-directed photons, while a second reverse-expander takes this collimated light and creates a more dense, collimated beam, the size of the optical fiber or smaller, on the photon entry end of the transmission fiber. The integrated lens is part of the bulb's glass, and is designed to operate at a far higher temperature than the layered glass used in a glass optical fiber.

Following the form of the calculations presented in the background section and Example 1, an optical fiber was initially modeled in the absence of lenses, attached to a 15 W lamp halogen lamp. In practice, increasing the wattage of the lamp increases the physical size of the filament and the distance of the fiber from the bulb, and does not result in better illumination of the fiber. At a conversion efficiency of 14% visible light output for halogen projection lamps operating at 3600 K, 12.9 W is lost as heat while 2.1 W is converted to visible light. For this example, we assume that the fiber is safe from damage when placed at a minimum 10 mm from the filament, and we assume use of a 100-micron diameter core fiber with a capture half-angle of 20 degrees. This fiber, as discussed in the background section, intercepts photons from the bulb over an area of 0.0079 mm$^2$ from a total sphere of uniform light 10 mm in diameter and with a surface area of 105 mm$^2$, for a transfer efficiency of 0.0078% (Table 4). Together with a conversion efficiency of 14%, this yields a net delivery efficiency of 0.0011%, with 0.16 mW delivered to the sample, and 82,000 mW of heat produced for each mW of light delivered. Despite the high heat production, this light source remains cool at the fiber end closest to the sample, and this fiber end can even be placed against delicate samples, such as if the fiber were to be deployed in a needle configuration. A high power density is achieved at the exit of the illumination fiber of 20.1 mW/mm$^2$, as shown below in Table 4.

Now, consider instead a lens-coupled bulb attached to a delivery fiber. The arrangement is as shown in FIG. 5, with a collimating lens placed 3 mm from the filament, and reverse expanders for capture of this collimated light into optical fibers. Modeling of this arrangement shows a significant improvement in the efficiency of light delivery, as shown in Table 4, below.

TABLE 4

Fiber-Based Coupling Without and With Integrated Transfer Lenses.

| Type of Light Source (fiber-coupled 10 mm from filament) | Conversion Effi ciency (%) | Coupling Effi- ciency (%) | De- livery Effi ciency (%) | Spot Density (mW/ mm$^2$) | Thermal Load (Heat Produced per mW Light Delivered) |
|---|---|---|---|---|---|
| Halogen Bulb w/o Lens | 14% | 0.0075% | 0.0011% | 20.1 | 82,000 mW |
| Halogen Bulb w/Lens | 14% | 0.0833% | 0.0117% | 223 | 7,400 mW |
| White LED w/lens | 25% | 75% | 18% | 36 | 675 mW |
| Improvement for Halogen Using Lens | 1× | 11× | 11× | 11× | 11× |

In the table above, use of an integrated transfer lens with a high-efficiency halogen bulb results in a 11-fold improvement in delivery efficiency, and therefore a 11-fold reduction in the power required, and heat produced, to achieve comparable illumination levels at the tissue target. In this case, the light source is coupled to the sample via an optical fiber, and therefore none of the heat in either case would be transmitted to the sample (though if the bulb is deployed in the handle of a probe, reduced heat remains advantageous). However, from power considerations, reduced power is helpful in situations in which power sources are limited, such as in a battery-operated device employed in fieldwork. Here, a reduced power source would offer a significant extension of battery life, as much as 11-fold longer life in this case.

Of practical importance, this model suggests that the light density of the spot exiting the fiber is higher with than without the transfer lenses. A high density is important when delivering light via fibers, either as illumination to an area via free-space coupling, as well as when there is an aperture limitation, such as a needle, into which as much light as possible is to be transmitted to the tissue sample. In such needles and probes, free space transfer from the bulb to the sample is not possible, and therefore light input to the sample is limited by the light density within the delivery optics.

Note that excess heat production impacts and reduces light production, as a hot light source necessitates that the lamp must then be moved farther from the sample, which in turn results in additional coupling losses which in further necessitate a higher powered bulb, and so on. However, once a decision is made to fiber-couple the source, the light densities achieved into the fiber via lens coupling will work to minimize the input power required to meet a achieve a given sample illumination output power at the sample end of the fiber.

Note also that for some bulb types, such as a halogen lamp, high heat output is an inherent requirement of proper bulb operation, as the bulb's internal glass surface temperature must be at 120–140° C. in order to allow for halogen recycling to occur, and for the filament to tolerate the high operating temperatures. However, again due to the high density of broadband light achievable, this may be the preferred option for needle-based probes.

Last, a white LED light source can be similarly connected via fiber, as will be tested in the following example.

Example 4

Measurement Using Fiber-Coupled Bulb with and without Transfer Lenses

In order to test the validity of the data generated using the lens-coupled fiber model shown in Example 3, we constructed four fiber-based test probes: two using halogen bulbs (with and without lens transfer optics), and two using a white LED (again, with and without transfer optics). We then tested these probes for the light density passed into the optical fiber, in order to calculate the true effect of the transfer lenses.

In these measurements, an optical fiber was illuminated using a bare 15 W halogen bulb run at 5.6 W, or with a 150 mW white LED run at 70 mW, each tested both with and without an integrated lens and external collimating optics. Light collected by the fiber was measured for overall intensity from 400 nm to 1100 nm using the silicon-based photodiode system used in Example 2. Results are shown in Table 5, below:

TABLE 5

Measured Improvement in Lens-Coupled Fiber Light Levels.

| | Halogen Lamp (mW/100 μm fiber) | White LED (mW/100 μm fiber) |
|---|---|---|
| No Lens | 0.12 mW | 0.0004 mW |
| With Lens and Collimator | 1.20 mW | 0.0181 mW |
| Improvement in Delivery Efficiency | 9.8× | 45.2× |

The above-measured improvements in delivery efficiency are, within experimental error, in agreement with the projected ratio of an 11-fold improvement. Of note, the spot density of the light from a halogen bulb, collected through an optical fiber, was 152 mW/mm$^2$, in agreement with Table 1 and up from 15.7 mW/mm$^2$ without the transfer lens optics. This yields an improvement of nearly 10-fold. For the white LED, the transfer optics generates a spot density of 2.3 mW/mm$^2$, which should rise to over 10 mW/mm$^2$ at higher operating currents. In the case of the LED, the improvement using transfer and coupling lenses was over 46 fold.

Importantly, we have again achieved a central goal of the improved illumination source: the ability to increase the efficiency of delivery to produce a higher-density, reduced thermal load source. In this case, we used improved coupling so that the density of the optical spot has been increased 10- to 46-fold (with a resulting spot density of at least 10 mW/mm$^2$, and potentially 100–500 mW/mm$^2$ or higher), while delivering this illumination through an insulating optical fiber such that the net heat delivery to the sample is negligible. Thus, the use of coupling lenses, to increased the transfer efficiency, coupled to fibers, to provide thermal insulation, has allowed construction of a biologically-safe illumination source achieving nearly the same density of light delivery as the deployment of a bulb directly into the probe, but without the danger that may come with such deployment of a hot bulb into the body or near a delicate sample.

Last, consider the interest in illuminating a 1 cm diameter area using light from either a 100 micron optical fiber versus direct illumination with a white LED. In such a case, the advantage of the white LED is clear, as shown in Table 6:

TABLE 6

Comparison of white LED and fiber illumination of 1 cm tissue region

| Type of Illuminator Source | Power (mW) | 1 cm Field Intensity (mW) | Delivery Efficiency | Thermal Load (mW Heat/Light/cm$^2$) |
|---|---|---|---|---|
| Halogen Bulb w/Fibers and Transfer Lenses | 9180 | 1.20 mW | 0.01% | 7400 |
| White LED w/Lens | 170 | 3.56 mW | 2.09% | 35 |
| Improvement of White LED over Halogen | 54× | 3.0× | 160× | 211× |

In the table above, use of a white LED, rather than a fiber-based illumination probe, has increased the delivery efficiency 160-fold, reduced power consumption 54-fold, without raising the transferable thermal load above a physiologically tolerable level.

Example 5

Monitoring Gastric Oxygenation Using a Lensed Fiber-Coupled Light Source.

Illuminators, constructed in accordance with the present invention, were tested in human and animal subjects with institutional animal and human review board approval, as appropriate.

The illuminator of FIG. 5 was incorporated into medical system 267. Fiber-optic-based catheter probe 403, designed for endoscopic use, was constructed as shown in FIG. 6. A connector 429 connects the catheter 403 to illuminator 347 via socket 333, with socket 333 and fiber 424 (335) receiving the illumination as shown in FIG. 5. On cross-sectional view, catheter 403 has core illumination fiber 424 and light return fiber 425, all contained within Teflon sheath 414 and tubing 417, 424 and 425 polished and exposed to the patient as fiber ends 434 and 437, respectively. Fiber ends 434 and 437 are held at a distance of 1 to 20 mm from the mucosal surface, and estimates of mucosal oxygenation are made through analysis of the light captured and returned along fiber 425, for example using the spectroscopic monitoring device disclosed in U.S. Pat. No. 6,167,297.

Catheter 403 was then used, under Human Internal Review Board approval, during collection of data from various regions of the esophagus, stomach, intestine, and colon in live human subjects.

Normal values were collected from multiple subjects. The results from 29 subjects, with multiple tests taken in most subjects, are summarized below in Table 7, as follows:

TABLE 7

Colon Oxygenation in 29 Human Subjects Using a Lens-Coupled Catheter.

| Location | Number of Subjects (N) | Total No. of Tests (M) | Mean +/− S.D. |
|---|---|---|---|
| Esophagus | 10 | 66 | 61% +/− 4% |
| Stomach | 10 | 121 | 64% +/− 5% |
| Cecum | 4 | 23 | 68% +/− 1% |
| Colon (proximal) | 10 | 67 | 65% +/− 4% |
| Colon (transverse) | 11 | 60 | 65% +/− 4% |
| Colon (distal, sigmoid) | 15 | 94 | 64% +/− 6% |
| Rectum | 18 | 161 | 66% +/− 3% |
| SUMMARY ALL REGIONS | 29 | 592 | 64% +/− 3% |

These gastrointestinal data show a high degree of correlation and a tight range of mucosal oxygenation values in the gastrointestinal tract of healthy human subjects. The tight standard deviation for human gastrointestinal mucosal tissue oxygenation suggests that this is a robust value in healthy subjects. For example, values in the colon or rectum below 60% (using this algorithm and analysis) are automatically more than 2 s.d. below the mean, should be considered as improbably low in normal colon tissue.

We further tested this probe under two conditions that alter tissue oxygenation and induce hypoxia: hypoxemia (low arterial blood saturation) and ischemia (normal arterial oxygenation with low oxygen delivery due to impaired blood flow or low hematocrit).

In hypoxemia, colon oxygenation as measured by the catheter was well correlated with pulse oximetry, as would be expected (r=0.99, data not shown).

In ischemia, produced by clamping of major arterial supply to the distal colon, the catheter was able to detect lowered arterial oxygenation despite an absence of deoxygenation of the arterial blood (not shown). Similar results are seen in the monitoring of small colon projections, called polyps, as the arterial blood supply was interrupted, and ischemia produced, by either injections of epinephrine or vascular tie-off. Ischemia was well detected by the catheter, without any effect from saline control injections, as follows:

TABLE 8

Colon Polyp Oxygenation During Ischemia

| Polyp Intervention | Oxygenation (Mean +/− SD) | No. of Tests |
|---|---|---|
| Normal | 63% +/− 6% | 26 |
| Vascular Tie-Off | 8% +/− 3% | 8 |
| Epinephrine Injection | 6% +/− 6% | 16 |
| Control (Saline Injection) | 68% +/− 2% | 4 |

As another example of ischemia, the average mucosal oxygen saturation standard deviation was 3.5%, as shown previously in Table 7. Table 9 (below) shows the measurement results from an asymptomatic 61-year-old patient who had undergone a partial colectomy 5 years previously for cancer (an adenocarcinoma). During the operation, 15 cm of sigmoid colon were resected and the inferior mesenteric artery was sacrificed and removed. The surveillance colonoscopy demonstrated an intact anastomosis of the rejoined colon sections, 25 cm from the rectum, with approximately 10 cm of normal-appearing sigmoid colon distal to the anastomosis. The measured mucosal saturation in the remaining portion of the sigmoid colon, which had been supplied by the inferior mesenteric artery, now removed, was 47%. This value is 17% below normal ($p<0.001$). In contrast, measurements in regions of the colon showed higher oxygenation values the farther from the sacrificed artery one measured. At some distance from the lost artery, where the colonic circulation had not been disturbed, the measured saturation values were normal. This is shown as follows:

TABLE 9

Saturation of colon in a man with a surgically interrupted inferior mesenteric artery (IMA).

| Region | Saturation |
|---|---|
| Ascending Colon | 63% |
| Transverse Colon | 65% |
| Anastomosis | 57%* |
| Sigmoid Colon | 49%* |
| Rectum | 61% |

*= p < 0.05
*= p < 0.001

As a final example of ischemia, there is a gradual and developing ischemia induced by injection of epinephrine into a polyp. In this case, an intervention (injection) has caused the flow of blood in the tissue to fall, leading to a gradual drop in oxygenation over time. Thus, the system can be used to monitor a medical intervention, and detect changes in oxygenation that warn of impending tissue injury. The drop in oxygenation after injection with epinephrine is shown in Table 10, as follows:

TABLE 10

Oxygenation falling in a polyp after an interventional injection of epinephrine. The oxygenation values fall after injection, falling to nearly zero after additional time has passed (not shown). The values do not fall completely to zero as a small amount of oxygen is absorbed from the air. After the tissue dies, the saturation values may rise, as oxygen is absorbed from the air, but it is no longer metabolized by the tissue.

| Time After Injection (sec) | Saturation (%) |
|---|---|
| Injection | 64% |
| 30 sec | 54% |
| 60 sec | 49% |
| 90 sec | 30% |
| 120 sec | 25% |
| 180 sec | 17% |

Thus, we have shown that a colon device could detect both hypoxemia and ischemia. The gastrointestinal tract is important as it is a central organ, and more closely approximates oxygen delivery to the body's core organs than does peripheral arterial oxygenation. Also, many interventional procedures affect gastrointestinal oxygenation, thus the ability to measure this value is likely to have medical value. Last, central organs are more likely to be less sensitive to motion, cold, and other factors that interfere with conventional oximetry. Sites of measurement in the gastrointestinal system could reasonably include the oropharynx, nasopharynx, esophagus, stomach, duodenum, ileum, colon, or other gastrointestinal tissues This system has multiple advantages over conventional pulse oximetry. First, the signal does not require a pulse in order to operate. Second, as the signal analyzed is not a pulse, but rather the full returning signal, the signal is inherently less noisy that the AC-extracted-from-total signal of pulse oximetry, in which the AC component tends to represent less than 1% of the total signal. Because of this, estimates for met-hemoglobin, carboxy-hemoglobin, and other blood components may be more easily accomplished.

In the above examples, the signal detected from the tissue was an absorbance signal. While absorbance is ideal for hemoglobin analysis, as described in the preferred embodiment, other interactions may be preferable for other measurements. The interaction with the illuminating light that provides the contrast can include absorbance, polarization, optical rotation, scattering, fluorescence, Raman effects, phosphorescence, or fluorescence decay, and measures of a contrast effect may reasonably include one or more of these effects. For example, a coronary artery catheter could use a dye to report on inflammation or hyperthermia, suggestive of unstable arterial plaque. This could occur by use of native emissions, or the signal could be enhanced, for example by detecting the presence of a dye which differentially accumulates in unstable plaque, or which exhibits a dye shift based upon temperature of the inflamed tissue.

Example 6

Measurement of Tissue Oxygenation Using White LED Probe

In order to further test the validity of the data generated using the model shown in Example 1, we constructed additional working probes based upon an embedded white LED as illustrated in FIG. 2 and FIG. 3.

In these experiments, we tested a human subject with a normal colon alternated between breathing room air and a helium mixture with reduced oxygen. During this procedure, colon oxygenation was monitored with the white-LED-based probe.

Figure 7:
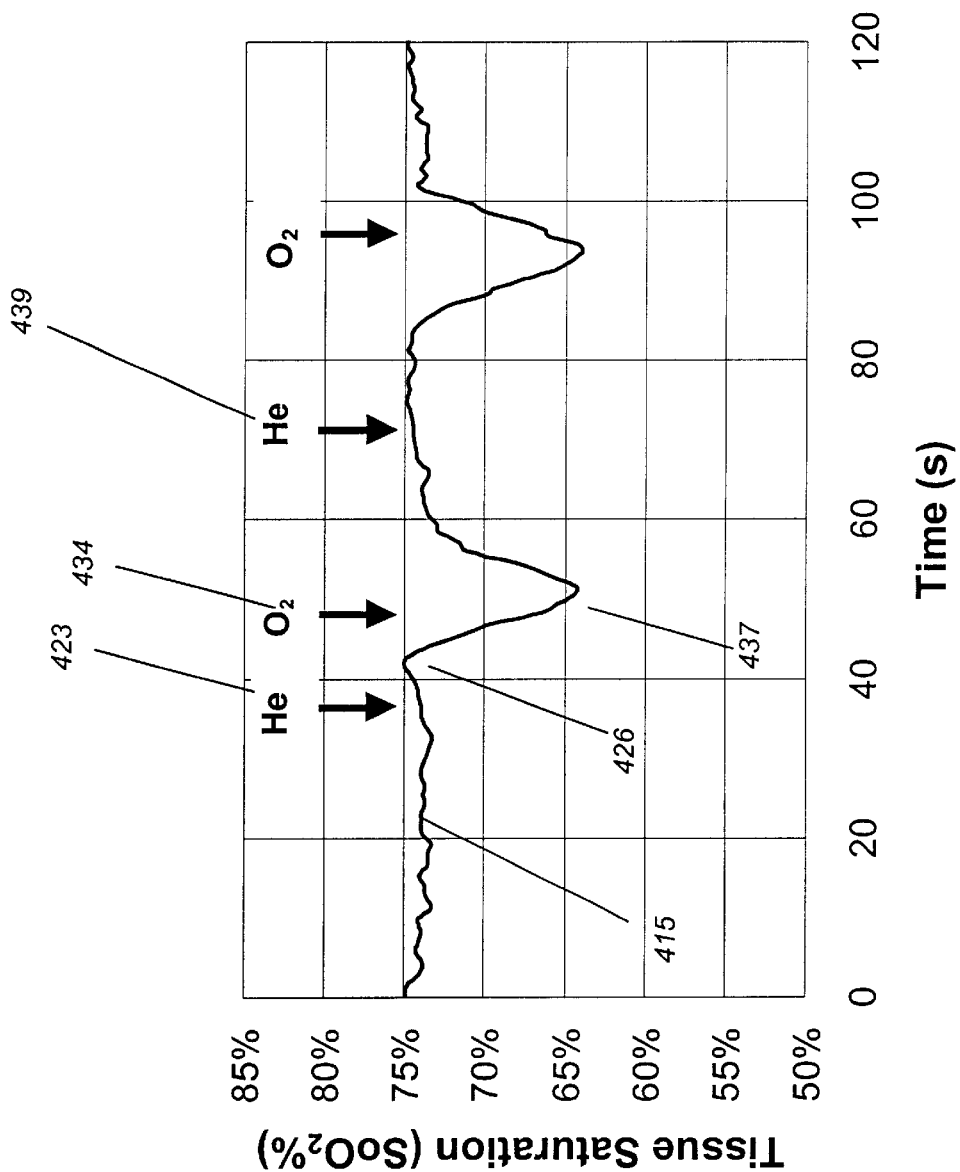
FIG. 7 shows data from the colon of a live human subject during periods of low arterial oxygen in vivo, as collected and analyzed in real time by a medical monitor to which the catheter of FIG. 6 is attached.

Results are shown in FIG. 7. Here colon optical saturation 415 begins within the normal range of values described earlier in Table 7. At time point 423, the subject inspires a helium mixture, and as a result, at time point 426 saturation 415 begins to fall from 74% to as low as 64%, demonstrating detection of hypoxemia. At time point 434, the subject inspires room air, and as a result, at time point 437 saturation 415 begins to recover to baseline. This pattern of detectable desaturation is repeated during a second episode of helium inspiration at time point 445.

Use of a white LED has several unexpected advantages. First, a white LED is very stable, even shortly after startup, in contrast to the majority of bulbs lamps that are inherently unstable. As a filament bulb warms up, the operating temperature, and thus the light output and color spectrum, shift. Time is required for the bulb to stabilize before spectroscopic measurements can be made, as the reference signal (the bulb spectrum) cannot be accurately measured when the bulb spectrum is changing (unless the reference itself is continuously sampled). Further, as a bulb ages, the tungsten filament evaporates onto the bulb glass, and changes the output. Many bulbs drop their output by over half during their lifetime. Thus, during long procedures, any bulb with a shortened life (under 1,000 hours) suffers from significant aging, and thus significant drift. Conversely, while it is possible that a light bulb can be made more temporally stable by lowering the electrical current, doing so increases the fraction of heat produced, dropping the luminous efficiency to under 2%. Last, arc-lamps sputter and flicker significantly during operation as a basic characteristic of operation. Another advantage is to allow incorporation into an integrated medical probe, device, or system, for performing real-time spectroscopy in living tissue in vivo. Another advantage is the high level of light delivered to a tissue region. Another advantage is that custom broadband LEDs can be made from polymers embedded with different fluorescent or phosphorescent agents, while white LEDs themselves are inexpensive. Still another advantage is that the power draw of an LED is so low that batteries could be permanently incorporated into the LED-based probes, reducing the complexity of the plug coming from the probe and returning to the medical system monitoring a medical or surgical procedure.

Example 7

Biocompatible Luminescence Based Source

The material in a white LED can be replaced with other fluors in order to provide a broadband LED with unique characteristics. For example, Lumigen™, TPB™ (TetraPhenylButadiene), quantum dots, and others, can be used to convert blue or UV luminescent light from a conventional LED into a broadband source. Further, significant knowledge exists regarding how to attach and prepare Lumigen™ within a manufactured product. Lumigen™ is approved by the U.S. F.D.A. for use in food containers, Lumigen™ can withstand 220° C., so it can be deposited on fibers and then illuminated to generate fluorescent light from a fiber, plastic fiber can be embedded with the Lumigen™ and can be polished, and Lumigen™ can be deposited dissolved in a hot spray.

In summary, improved illuminators with multiple expected and unexpected advantages can therefore result from improving the delivery efficiency of light from spectroscopic light sources to target regions or samples. In certain applications, such as medical applications or microchip spectrophotometers, this improvement may need to occur without transferring undue heat to the sample and/or occur under space and size constraints, all without degrading or with improvement in output stability. We show that improved delivery can be achieved by either (a) improving the conversion efficiency of the source, which results in less heat per unit energy consumed, as well as less heat produced for any given level of desired light delivery to the tissue, or (b) improving the transfer efficiency of light from the source to the sample or tissue, such as by improving the coupling efficiency of light to a light guide or by sufficiently improving the conversion efficiency to allow the light source to be sufficiently cool to be embedded directly next to the sample, or both (a) and (b) together, such that the improved illuminator can even be embedded into a medical probe or microchip spectrophotometer. Higher efficiency delivery results in a cooler, more efficient light source, as fewer watts of power are required to produce a given level of illumination at the sample. An added benefit is that cooler sources tend to be more stable, simplifying measurements (by allowing for a single or pre-measured reference), improving data quality (by reducing reference error and sampling drift). Such improved illuminators may permit a light source to be embedded into a device, such as into a medical probe, catheter, or monitor, as well as into a microchip analysis system.

We have discovered an improved illumination source for generating broadband light, and for delivering this light to a sample, with higher efficiency, and possibly with higher optical density, than is achieved using conventional barebulb or fiber-coupled light sources, for the purpose of enabling spectroscopic analysis. A illuminator probe has been constructed and tested, in which a phosphor-coated white LED and integrated collimating optics have been constructed in accordance with the present invention to produce continuous, broadband light from 400 nm to 700 nm in a collimated beam, which can then be transmitted through space to a sample, such as a target tissue, resulting in a high efficiency delivery of light to the target region. The efficient conversion of power to light, and the high efficiency of light transfer, allow this illuminator to remain cool during operation despite high illumination levels, further permitting the illuminator to be integrated into the tip of a medical instrument, where then broadband illuminator can illuminate living tissue without damaging the tissue. Scattered light, returning from the sample, is optionally collected by an optical fiber integrated within the source optics of the illuminator, for transfer and analysis. Medical probes and systems incorporating the improved illuminator, and medical methods of use, are described. This device has been built and tested in several configurations in models, animals, and humans, and has immediate application to several important problems, both medical and industrial, and thus constitutes an important advance in the art.

What is claimed is:

1. An improved broadband spectroscopy illuminator comprising:

a broadband light source and an optical coupling means for coupling the light source to a target region, said source and optical coupling means configured and arranged to achieve an improved efficiency of delivery to said region with a high optical density of at least 1 mW/cm$^2$ and a low transferable thermal load of no more than 100 mW heat per mW usable optical power delivered.

2. The illuminator of claim 1, wherein said light source is a high conversion efficiency light source selected to operate with a typical conversion efficiency of at least 15%, said improved efficiency of delivery resulting at least in part from said high conversion efficiency.

3. The illuminator of claim 1 or 2, wherein said light source comprises a broadband LED.

4. The illuminator of claim 3, wherein said light source comprises a white LED.

5. The illuminator of claim 3 wherein said broadband LED comprises an LED coupled to a broadband emitting phosphor.

6. The illuminator of claim 1 or 2, wherein said light source comprises a blue LED optically coupled to a blue absorbing phosphor reservoir.

7. The illuminator of claim 1, wherein said coupling means includes transfer optics selected and arranged so as to achieve an improvement in transfer efficiency of at least 2-fold, as compared to a transfer efficiency of said illuminator in the absence of said transfer optics, said improved efficiency of delivery at least in part a result of said improved transfer efficiency.

8. The illuminator of claim 7, wherein said transfer optics includes at least one collimation lens.

9. The illuminator of claim 8, wherein said broadband light source comprises a lamp having a bulb and said at least one collimation lens is integral to the bulb of the lamp, said collimation lens arranged to have its proximal surface located no more than 10 mm from the source of said light within said lamp.

10. The illuminator of claim 7, wherein said transfer optics includes at least one refocusing lens.

11. The illuminator of claim 10, wherein said coupling means includes an optical fiber, and said refocusing lens is focused on the illumination end of said optical fiber.

12. The illuminator of claim 7, wherein said broadband light source is fiber-coupled to said target region, said coupling means includes at least one thermally-insulating optical fiber, said fiber is proximally optically coupled to said source and distally optically coupled to said target region.

13. The illuminator of claim 12, wherein said source comprises a halogen recycle filament bulb lamp, said coupling means comprises a collimating lens optically coupled to the filament and a reverse beam expander optically coupled to the collimating lens, said collimating lens integral to the bulb of said lamp and arranged to have its proximal surface located no more than 10 mm from the filament of said lamp, and said reverse expander further optically coupled to said optical fiber.

14. The illuminator of claim 1, wherein said illuminator is further arranged so as to be removably optically coupled to a medical probe.

15. The illuminator of claim 1, wherein said illuminator is further incorporated into the body of a medical probe.

16. The illuminator of claim 1, wherein said illuminator is further incorporated into the patient end of a medical probe.

17. The illuminator of claim 14, 15, or 16 wherein said medical probe is selected from the list of medical probes consisting of catheters, sheaths, guidewires, needles, trocars, surgical instruments, and injection probes.

18. The illuminator of claim 1, wherein said illuminator is further incorporated into a medical system.

19. The illuminator of claim 1, wherein said illuminator further comprises a light collection fiber, said light collection fiber integrated into said illuminator and optically coupled to said target region.

20. A medical illuminator catheter comprising:

(a) a biocompatible catheter sheath, said catheter sheath having a monitor end, a central body, and a patient end;

(b) a mixed optical and electrical connection plug, said plug located at or near the monitor end of said catheter;

(c) an integral broadband light source for illuminating a target region and a collimating transfer lens for optically coupling said source to said region over free space, said source and lens integrated into said body of said catheter, said source and lens further selected and arranged so as to deliver to said region an optical density of at least 1 mW/cm$^2$ over said target region with a transferable thermal load of no more than 100 mW heat per mW usable optical power delivered;

(d) an optical collection fiber for collecting light scattered from said target region and for transmitting said collected light from said patient end of the catheter, along a length of said catheter, to a said connection plug at or near said monitor end of the catheter, and, (e) power supply wires for transmitting electrical power to said light source, said wires traversing a length of said catheter and electrically connected to both said light source and said connection plug.

21. The illuminator catheter of claim 20, further including a battery, said battery integrated into the body of said catheter.

22. The illuminator catheter of claim 21, further including a power switch for switching said illuminator off and on.

23. The illuminator catheter of claim 20, further including an information storage device, for storing information related to the catheter function, serial number, and use history.

24. An illuminator catheter comprising:

(a) a biocompatible catheter sheath, said catheter sheath having a monitor end, a central body, and a patient end;

(b) an optical connection plug, said plug located at or near the monitor end of said catheter;

(c) an integral broadband LED light source for illuminating a target region and a collimating transfer lens for optically coupling said source to said region over free space, said source and lens integrated into said body of said catheter;

(d) a power source;

(e) an optical collection fiber for collecting light scattered from said target region and for transmitting said collected light from said patient end of the catheter, along a length of said catheter, to said connection plug, and, (f) power supply wires for transmitting electrical power from said power source to said light source, said wires traversing a length of said catheter from said power source to said light source.

25. The illuminator of claim 24, wherein said broadband light source is a broadband LED.

26. An illuminator catheter as in claim 24 in which the power source is located at or near the monitor end of said catheter.

27. The illuminator device of claim 26, wherein the connector plug is a mixed optical and electrical connection plug.

28. The illuminator device of claim 24, wherein said broadband light source is a white LED.

29. The illuminator catheter of claim 24, wherein said power source comprises a battery integrated into the body of said catheter.

30. The illuminator catheter of claim 24, further including a power switch for switching power to said light source.

31. The illuminator catheter of claim 24, further including an integral information storage device, for storing information related to the catheter function, serial number, and use history.

32. The illuminator of claim 24, wherein said light source is further incorporated into a lab-on-a-chip system.

* * * * *

(12) INTER PARTES REEXAMINATION CERTIFICATE (0257th)
United States Patent
Benaron et al.

(10) Number: US 6,711,426 C1
(45) Certificate Issued: Apr. 19, 2011

(54) SPECTROSCOPY ILLUMINATOR WITH IMPROVED DELIVERY EFFICIENCY FOR HIGH OPTICAL DENSITY AND REDUCED THERMAL LOAD

(75) Inventors: David A. Benaron, Portola Valley, CA (US); Ilian H. Parachikov, Fremont, CA (US)

(73) Assignee: Spectros Corporation, Portola Valley, CA (US)

Reexamination Request:
No. 95/001,232, Sep. 15, 2009

Reexamination Certificate for:
Patent No.: 6,711,426
Issued: Mar. 23, 2004
Appl. No.: 10/119,998
Filed: Apr. 9, 2002

(51) Int. Cl.
*A61B 5/00* (2006.01)
*A61B 1/06* (2006.01)
*G02B 6/06* (2006.01)

(52) U.S. Cl. .................... 600/342; 600/478; 362/572
(58) Field of Classification Search .................. None
See application file for complete search history.

(56) References Cited

U.S. PATENT DOCUMENTS

| | | | |
|---|---|---|---|
| RE29,304 E | 7/1977 | Greenfield et al. | |
| 4,164,374 A | 8/1979 | Lambe et al. | |
| 4,213,462 A | 7/1980 | Sato | |
| 4,427,889 A | 1/1984 | Müller | |

(Continued)

FOREIGN PATENT DOCUMENTS

| | | |
|---|---|---|
| EP | 1 111 333 A1 | 6/2001 |
| EP | 1 126 402 A2 | 8/2001 |
| EP | 1 094 746 B1 | 10/2002 |
| EP | 0 926 981 B1 | 3/2004 |
| GB | 2357856 A | 4/2001 |
| JP | 05-152609 | 6/1993 |
| WO | WO 00/64534 A1 | 11/2000 |
| WO | WO 01/01070 A1 | 4/2001 |
| WO | WO 03/003914 A1 | 1/2003 |

OTHER PUBLICATIONS

Shimazaki et al., "A Portable Spectrophotometer Using a White–Color Light–Emitting Diode and a Charge–Coupled Device and Its Application to On–Site Determination of Iron," Analytical Sciences, Oct. 2000, vol. 16, The Japan Society for Analytical Chemistry, pp. 1091–1093.

Bogner et al., "White Light LED," SPIE vol. 3621, pp. 143–, SPIE Conference on Light–Emitting Diodes, Research, Manufacturing and Applications III, San Jose, CA, Jan. 1999, pp. 143–150.

Shuji Nakamura, "Present performance of InGaN based blue/green/yellow LEDs," SPIE vol. 3002, 0277–786X/97 (1997), pp. 26–35.

Kitamura et al., "Optical constants of silica glass from extreme ultraviolet to far infrared at near room temperature," Applied Optics, vol. 46, No. 33 (2007), pp. 8118–8131.

Ikeda, K., et al., "Improvement of Photo–Electric Plethysmograph Applying Newly Developed Opto–Electronic Devices, "IEEE Tencon, 1999, pp. 1109–1112.

*Primary Examiner* — Jeffrey R. Jastrzab

(57) ABSTRACT

An improved illuminator for generating broadband light, and for delivering the light to a sample with an improved delivery efficiency, for higher optical density and/or reduced thermal transfer, than achieved with conventional halogen bulb sources. The illuminator enables spectroscopic analysis in thermally-sensitive or spatially-constrained environments. A phosphor-coated broadband white LED and integrated collimating optics produces a continuous, collimated broadband light beam from 400 nm to 700 nm, which is then transmitted through space to a sample region, such as a living tissue in vivo. This results in a high net efficient delivery of light to the tissue sample. An efficient conversion of power to light, and the high delivery efficiency, keeps both the illuminator and sample cool during operation, allowing the illuminator to be integrated into the tip of a medical probe or into monitoring systems.

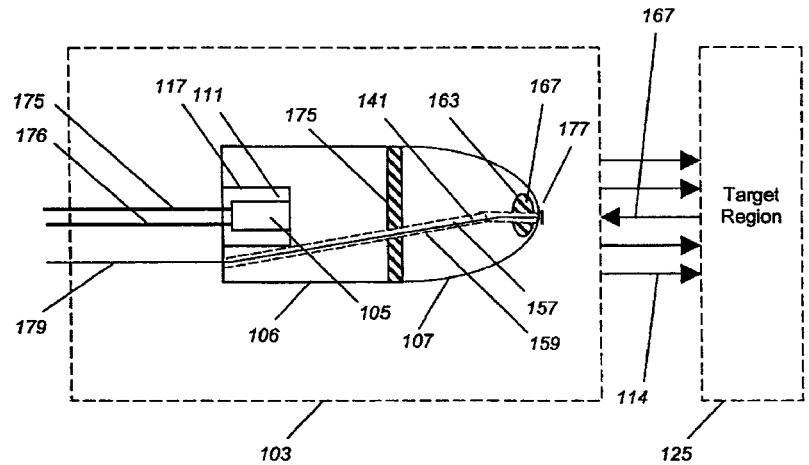

U.S. PATENT DOCUMENTS

| | | | |
|---|---|---|---|
| 4,513,751 A | 4/1985 | Abe et al. |
| 4,697,593 A | 10/1987 | Evans et al. |
| 5,040,533 A | 8/1991 | Fearnot |
| 5,040,538 A | 8/1991 | Mortazavi |
| 5,135,004 A | 8/1992 | Adams et al. |
| 5,190,040 A | 3/1993 | Aoyagi |
| 5,199,428 A | 4/1993 | Obel et al. |
| 5,259,052 A | 11/1993 | Briggs et al. |
| 5,318,022 A | 6/1994 | Taboada et al. |
| 5,329,922 A | 7/1994 | Atlee, III |
| 5,357,954 A | 10/1994 | Shigezawa et al. |
| 5,417,207 A | 5/1995 | Young et al. |
| 5,520,190 A | 5/1996 | Benedict et al. |
| 5,672,875 A | 9/1997 | Block et al. |
| 5,696,861 A | 12/1997 | Schimmeyer et al. |
| 5,733,313 A | 3/1998 | Barreras, Sr. et al. |
| 5,743,261 A | 4/1998 | Mainiero et al. |
| 5,769,791 A | 6/1998 | Benaron et al. |
| 5,777,350 A | 7/1998 | Nakamura et al. |
| 5,779,631 A | 7/1998 | Chance |
| 5,785,658 A | 7/1998 | Benaron et al. |
| 5,830,132 A | 11/1998 | Robinson |
| 5,830,137 A | 11/1998 | Scharf |
| 5,833,603 A | 11/1998 | Kovacs et al. |
| 5,902,235 A | 5/1999 | Lewis et al. |
| 5,933,498 A | 8/1999 | Schneck et al. |
| 5,987,346 A | 11/1999 | Benaron et al. |
| 6,043,893 A | 3/2000 | Treiman et al. |
| 6,119,031 A | 9/2000 | Crowley |
| 6,122,536 A | 9/2000 | Sun et al. |
| 6,127,783 A | 10/2000 | Pashley et al. |
| 6,134,460 A | 10/2000 | Chance |
| 6,167,297 A | 12/2000 | Benaron |
| 6,216,021 B1 | 4/2001 | Franceschini et al. |
| 6,226,082 B1 | 5/2001 | Roe |
| 6,256,524 B1 | 7/2001 | Walker et al. |
| 6,277,078 B1 | 8/2001 | Porat et al. |
| 6,278,889 B1 | 8/2001 | Robinson |
| 6,331,156 B1 | 12/2001 | Haefele et al. |
| 6,353,226 B1 | 3/2002 | Khalil et al. |
| 6,381,018 B1 | 4/2002 | Bigio et al. |
| 6,432,364 B1 | 8/2002 | Negami et al. |
| 6,527,729 B1 | 3/2003 | Turcott |
| 6,532,381 B2 | 3/2003 | Bayer et al. |
| 6,533,466 B1 | 3/2003 | Smith |
| 6,550,979 B1 | 4/2003 | Fleenor et al. |
| 6,588,938 B1 | 7/2003 | Lampert et al. |
| 6,599,025 B1 | 7/2003 | Deutsch |
| 6,612,857 B2 | 9/2003 | Tolmie |
| 6,615,065 B1 | 9/2003 | Barrett et al. |
| 6,662,033 B2 | 12/2003 | Casciani et al. |
| 6,694,159 B2 | 2/2004 | Hall et al. |
| 6,744,514 B2 | 6/2004 | Kemmler et al. |
| 6,842,635 B1 | 1/2005 | Parker |
| 6,859,658 B1 | 2/2005 | Krug |
| 6,921,920 B2 | 7/2005 | Kazakevich |
| 7,062,306 B2 | 6/2006 | Benaron et al. |
| 2002/0082488 A1 | 6/2002 | Al-Ali et al. |
| 2003/0111533 A1 | 6/2003 | Chang |
| 2005/0010113 A1 | 1/2005 | Hall et al. |

INTER PARTES REEXAMINATION CERTIFICATE ISSUED UNDER 35 U.S.C. 316

THE PATENT IS HEREBY AMENDED AS INDICATED BELOW.

AS A RESULT OF REEXAMINATION, IT HAS BEEN DETERMINED THAT:

The patentability of claims 11-23 is confirmed.

Claims 1-10 and 24-32 are cancelled.

\* \* \* \* \*

(12) INTER PARTES REEXAMINATION CERTIFICATE (494th)
United States Patent
Benaron et al.

(10) Number: US 6,711,426 C2
(45) Certificate Issued: Dec. 14, 2012

(54) SPECTROSCOPY ILLUMINATOR WITH IMPROVED DELIVERY EFFICIENCY FOR HIGH OPTICAL DENSITY AND REDUCED THERMAL LOAD

(75) Inventors: David A. Benaron, Portola Valley, CA (US); Ilian H. Parachikov, Fremont, CA (US)

(73) Assignee: Spectros Corporation, Portola Valley, CA (US)

Reexamination Request:
No. 95/001,688, Jul. 28, 2011

Reexamination Certificate for:
Patent No.: 6,711,426
Issued: Mar. 23, 2004
Appl. No.: 10/119,998
Filed: Apr. 9, 2002

Reexamination Certificate C1 6,711,426 issued Apr. 19, 2011

(51) Int. Cl.
*A61B 5/00* (2006.01)
*A61B 1/06* (2006.01)
*A61B 6/06* (2006.01)

(52) U.S. Cl. .................... 600/342; 600/478; 362/572
(58) Field of Classification Search .................. None
See application file for complete search history.

(56) References Cited

To view the complete listing of prior art documents cited during the proceeding for Reexamination Control Number 95/001,688, please refer to the USPTO's public Patent Application Information Retrieval (PAIR) system under the Display References tab.

*Primary Examiner* — Jeanne M Clark

(57) ABSTRACT

As improved illuminator for generating broadband light, and for delivering the light to a sample with an improved delivery efficiency, for higher optical density and/or reduced thermal transfer, than achieved with conventional halogen bulb sources. The illuminator enables spectroscopic analysis in thermally-sensitive or spatially-constrained environments. A phospor-coated broadband white LED and integrated collimating optics produces a continuous, collimated broadband light beam from 400 mm to 700 nm, which is then transmitted through space to a sample region, such as a living tissue in vivo. This results in a high net efficient delivery of light to the tissue sample. An efficient conversion of power to light, and the high delivery efficiency, keeps both the illuminator and sample cool during operation, allowing the illuminator to be integrated into the tip of a medical probe or into monitoring systems.

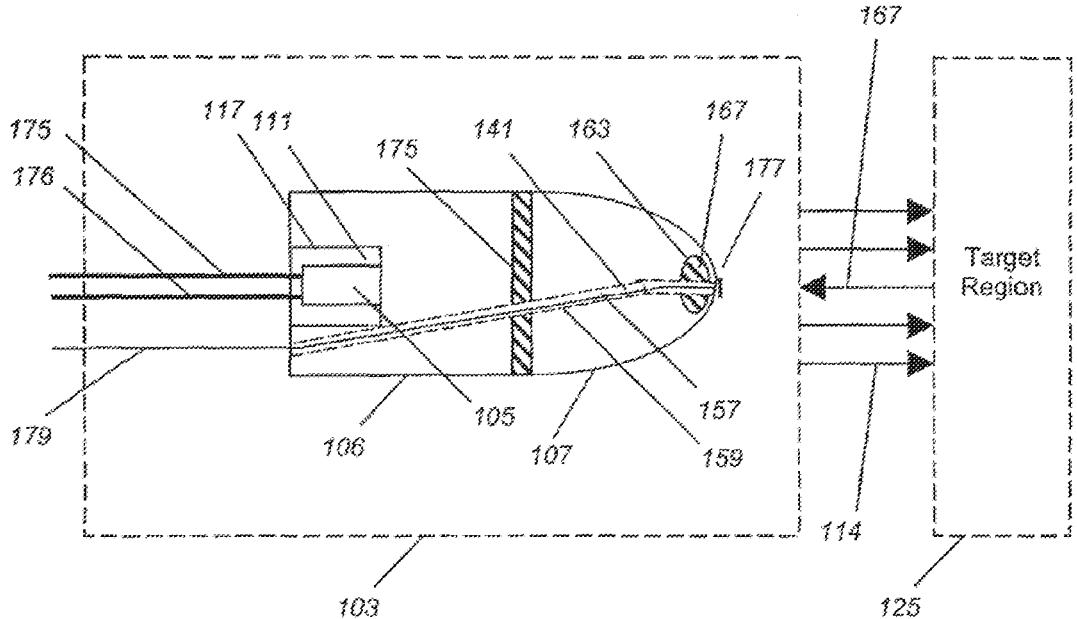

INTER PARTES REEXAMINATION CERTIFICATE ISSUED UNDER 35 U.S.C. 316

THE PATENT IS HEREBY AMENDED AS INDICATED BELOW.

AS A RESULT OF REEXAMINATION, IT HAS BEEN DETERMINED THAT:

Claims 1-10 and 24-32 were previously cancelled.
Claim 19 is cancelled.
Claims 11-18 and 20-23 were not reexamined.

* * * * *